(12) United States Patent
Parren et al.

(10) Patent No.: US 11,795,214 B2
(45) Date of Patent: Oct. 24, 2023

(54) MODULATION OF COMPLEMENT-DEPENDENT CYTOTOXICITY THROUGH MODIFICATIONS OF THE C-TERMINUS OF ANTIBODY HEAVY CHAINS

(71) Applicant: GENMAB A/S, Copenhagen V (DK)

(72) Inventors: Paul Parren, Odijk (NL); Patrick Van Berkel, Utrecht (NL); Ewald Van Den Bremer, Eindhoven (NL)

(73) Assignee: GENMAB A/S, Valby (DK)

(*) Notice: Subject to any disclaimer, the term of this patent is extended or adjusted under 35 U.S.C. 154(b) by 51 days.

(21) Appl. No.: 16/399,424

(22) Filed: Apr. 30, 2019

(65) Prior Publication Data

US 2020/0131253 A1   Apr. 30, 2020

Related U.S. Application Data

(62) Division of application No. 14/130,580, filed as application No. PCT/EP2012/063338 on Jul. 6, 2012, now Pat. No. 10,323,081.

(60) Provisional application No. 61/504,987, filed on Jul. 6, 2011.

(30) Foreign Application Priority Data

Jul. 6, 2011 (DK) .......................... PA 2011 00518

(51) Int. Cl.
| | | |
|---|---|---|
| C07K 16/18 | (2006.01) | |
| C07K 16/00 | (2006.01) | |
| G01N 33/50 | (2006.01) | |
| G01N 33/68 | (2006.01) | |

(52) U.S. Cl.
CPC .............. *C07K 16/18* (2013.01); *C07K 16/00* (2013.01); *G01N 33/5014* (2013.01); *G01N 33/6854* (2013.01); *C07K 2317/51* (2013.01); *C07K 2317/52* (2013.01); *C07K 2317/71* (2013.01); *C07K 2317/72* (2013.01); *C07K 2317/734* (2013.01)

(58) Field of Classification Search
CPC ............ G01N 33/6854; C07K 2317/51; C07K 2317/52; C07K 2317/71; C07K 2317/734
USPC ...................................................... 424/133.1
See application file for complete search history.

(56) References Cited

U.S. PATENT DOCUMENTS

| | | | |
|---|---|---|---|
| 9,320,812 B2 | 4/2016 | Hampl et al. | |
| 9,409,995 B2 | 8/2016 | Foord et al. | |
| 9,458,231 B2 | 10/2016 | Dylla et al. | |
| 10,323,081 B2 | 6/2019 | Parren et al. | |
| 11,059,908 B2 * | 7/2021 | Huh .......................... | A61P 3/06 |
| 2010/0260706 A1 * | 10/2010 | Bogin ..................... | A61P 25/14 |
| | | | 424/85.2 |
| 2010/0297697 A1 | 11/2010 | Ambrosius et al. | |
| 2013/0058947 A1 | 3/2013 | Stull et al. | |
| 2013/0224191 A1 | 8/2013 | Stull et al. | |
| 2013/0302355 A1 | 11/2013 | Dylla et al. | |
| 2014/0093495 A1 | 4/2014 | Hampl et al. | |
| 2014/0105888 A1 | 4/2014 | Foord et al. | |
| 2014/0271623 A1 | 9/2014 | Parren et al. | |
| 2014/0302034 A1 | 10/2014 | Bankovich et al. | |
| 2014/0303356 A1 | 10/2014 | Gramer et al. | |
| 2015/0322166 A1 | 11/2015 | Stull et al. | |
| 2016/0046722 A1 | 2/2016 | Chevreux et al. | |
| 2016/0257745 A1 | 9/2016 | Hampl et al. | |
| 2016/0264653 A1 | 9/2016 | Hampl et al. | |
| 2016/0272723 A1 | 9/2016 | Foord et al. | |
| 2019/0276549 A1 * | 9/2019 | De Jong ................. | A61P 29/00 |
| 2020/0181277 A1 * | 6/2020 | Beurskens .......... | C07K 16/2893 |
| 2021/0163619 A1 * | 6/2021 | Parren ................ | C07K 16/2896 |
| 2021/0371544 A1 * | 12/2021 | Huh ................... | C07K 16/2869 |

FOREIGN PATENT DOCUMENTS

| | | |
|---|---|---|
| WO | 2007/087420 A2 | 8/2007 |
| WO | 2007/106707 A2 | 9/2007 |
| WO | 2008/006554 A2 | 1/2008 |
| WO | 2009027471 A1 | 3/2009 |

OTHER PUBLICATIONS

Van den Bremer et al. (mAbs 7:4, 672-680; Jul./Aug. 2015).*
Markert et al. (Protein Engineering vol. 16 No. 12 pp. 1041±1046, 2003).*
Antes, B. et al., "Analysis of lysine clipping of a humanized Lewis-Y specific IgG antibody and its relation to Fc-mediated effector function," J Chromatogr B Analyt Technol Biomed Life Sci.,vol. 852: 250-256 (2007).
Betenbaugh M.J. et al., "Biosynthesis of human type N-glycans in heterologous systems," Current Opinion in Structural Biology, Elsevier Ltd., vol. 14(5):601-606 (2004).
Beurskens, F. J., et al., Exhaustion of cytotoxic effector systems may limit monoclonal antibody-based immunotherapy in cancer patients. J Immunol., vol. 188: 3532-3541 (2012).
Brunhouse, R. et al., "Isotypes of IgG: Comparison of the Primary Structures of three Pairs of isotypes which differ in their Ability to Activate Complement," Molecular Immunology, pergamon, GB., vol. 16(11):907-917 (1979).

(Continued)

*Primary Examiner* — Lynn A Bristol
(74) *Attorney, Agent, or Firm* — Nelson Mullins Riley & Scarborough LLP; Jane E. Remillard, Esq.; Christopher L. Frank

(57) ABSTRACT

Antibody variants having decreased or increased ability to mediate CDC due to modifications at the C-terminus of their heavy chains are described. Methods of generating such antibodies, as well as nucleotide constructs and host cells suitable for the production of said antibodies are also described.

23 Claims, 5 Drawing Sheets
Specification includes a Sequence Listing.

(56) References Cited

OTHER PUBLICATIONS

Burton, D. R., "Antibody: the flexible adaptor molecule" Trends Biochem Sci., vol. 15: 64-69 (1990).
Cai, B. et al., "C-terminal lysine processing of human immunoglobulin G2 heavy chain in vivo," Biotechnol Bioeng., vol. 108: 404-412 (2011).
Carter, P. J., "Potent antibody therapeutics by design," Nat Rev Immunol., vol. 6: 343-357 (2006).
Chappel, M. S., et al., "Identification of the Fc gamma receptor class I binding site in human IgG through the use of recombinant IgG1/IgG2 hybrid and point-mutated antibodies," Proc Natl Acad Sci U S A, vol. 88: 9036-9040 (1991).
Choi, B-K et al., "Use of Combinational Genetic Libraries to Humanize N-linked Glycosylation in the yeast *Pichia pastoris*," PNAS, vol. 100 (9): 5022-5027 (2003).
Chowdhury, P.S. et al., "Tailor-made Antibody Therapeutics Methods," A Companion to Methods in Enzymology, Academic Press Inc., US; vol. 36 (1): 11-24(2005).
Decker, E. L., et al., "Moss bioreactors producing improved biopharmaceuticals," Curr Opin Biotechnol., vol. 18: 393-398 (2007).
Dick, L. W., Jr., et al., "C-terminal lysine variants in fully human monoclonal antibodies: investigation of test methods and possible causes," Biotechnol Bioeng., vol. 100: 1132-1143 (2008).
Filpula et. al., "Antibody Engineering and Modification Technologies," Biomolecular Engineering, Elsevier, US, vol. 24(2):201-215 (2007).
Gramer, M. J. et al., "Product quality considerations for mammalian cell culture process development and manufacturing," Adv Biochem Eng Biotechnol., vol. 139: 123-166 (2014).
Hamilton, S. R., et al., "Glycosylation engineering in yeast: the advent of fully humanized yeast," Curr Opin Biotechnol., vol. 18: 387-392 (2007).
Hamilton, S. R., et al., "Production of complex human glycoproteins in yeast," Science, vol. 301: 1244-1246 (2003).
Harris, R. J., "Processing of C-terminal lysine and arginine residues of proteins isolated from mammalian cell culture," J Chromatogr A ., vol. 705: 129-134 (1995).
Harris, R. J., et al., "Identification of multiple sources of charge heterogeneity in a recombinant antibody," J Chromatogr B Biomed Sci Appl., vol. 752: 233-245 (2001).
Harris, R. J., et al., "Structural characterization of a recombinant CD4-IgG hybrid molecule," Eur J Biochem., vol. 194: 611-620 (1990).
Jefferies R., "Glycosylation as a strategy to improve antibody-based therapeutics," Nature Reviews, Drug Discovery Nature Publishing Group, vol. 8(3):226-234 (2009 ).
Khawli, L. A., et al., "Charge variants in IgG1: Isolation, characterization, in vitro binding properties and pharmacokinetics in rats," MAbs, vol. 2: 613-624 (2010).
Liu, H., et al., "Heterogeneity of monoclonal antibodies," J Pharm Sci., vol. 97: 2426-2447 (2008).
Luo, J., et al., "Probing of C-terminal lysine variation in a recombinant monoclonal antibody production using Chinese hamster ovary cells with chemically defined media," Biotechnol Bioeng., vol. 109: 2306-2315. (2012).
Moore, G. L., et al., "Engineered Fc variant antibodies with enhanced ability to recruit complement and mediate effector functions," MAbs, vol. 2: 181-189 (2010).
Pawluczkowycz, A. W., et al., "Binding of submaximal C1q promotes complement-dependent cytotoxicity (CDC) of B cells opsonized with anti-CD20 mAbs ofatumumab (OFA) or rituximab (RTX): considerably higher levels of CDC are induced by OFA than by RTX," J Immunol., vol. 183: 749-758 (2009).
Potgieter, T. et al., "Production of Monoclonal Antibodies by Glycoengineered Pichia pastoris," Journal of Biotechnology, vol. 139:318-325 (2009).
Raju, T. S., "Terminal sugars of Fc glycans influence antibody effector functions of IgGs," Curr Opin Immunol., vol. 20: 471-478 (2008).
Saphire, E. O., et al. "Crystal structure of a neutralizing human IGG against HIV-1: a template for vaccine design," Science, vol. 293: 1155-1159 (2001).
Schahs, M. et al., "Production of a Monoclonal Antibody in Plants with a Humanized N-glycosylation Pattern," Plant Biotechnology Journal, vol. 5:657-663 (2007).
Schuster, M., W. et al., "In vivo glyco-engineered antibody with improved lytic potential produced by an innovative non-mammalian expression system," Biotechnol J., vol. 2: 700-708 (2007).
Sliwkowski, M. X., et al. "Antibody therapeutics in cancer," Science, vol. 341: 1192-1198 (2013).
Strohl, W.R., "Optimization of Fc-mediated effector functions of monoclonal antibodies," Curr. Opin. Biotechnol., vol. 20:685-691 (2009).
Tang, L., et al., "Conformational characterization of the charge variants of a human IgG1 monoclonal antibody using H/D exchange mass spectrometry," MAbs, vol. 5: 114-125 (2013).
Teeling, J. L., et al., "Characterization of new human CD20 monoclonal antibodies with potent cytolytic activity against non-Hodgkin lymphomas," Blood, vol. 104: 1793-1800 (2004).
Wang, L. et al., "Structural Characterization of a Recombinant Monoclonal Antibody by Electrospray Time-of-Flight Mass Spectometry," Pharmaceutical Research, Kluwer Academic Publishers Plenum Publishers, vol. 22(8): 1338-1349 (2005).
Yang, J. M., et al., "Investigation of the correlation between charge and glycosylation of IgG1 variants by liquid chromatography-mass spectrometry," Anal Biochem., vol. 448: 82-91 (2014).
Yoshimi et al., "Inhibition of N-Linked Glycosylation Causes Apoptosis in Hamster BHK21 Cells," Biochemical and Biophysical Research Communications, vol. 276: 965-969 (2000).
Hu , Z. et al., "Carboxypeptidase D is the only enzyme responsible for antibody C-terminal lysine cleavage in Chinese hamster ovary (CHO) cells," Biotechnology and Bioengineering, vol. 113(10): 2100-210 (2016).
Liu, H. et al., "In vitro and in vivo modifications of recombinant and human IgG antibodies," mAbs, vol. 6(5):1145-1154 (2014).
Van den Brenner, E. et al. "Human IgG is produced in a pro-form that requires clipping of C-terminal lysines for maximal complement activation," mAbs, vol. 7(4):672-680 (2015).

* cited by examiner

SEQUENCE LISTING

<160> NUMBER OF SEQ ID NOS: 8

<210> SEQ ID NO 1
<211> LENGTH: 330
<212> TYPE: PRT
<213> ORGANISM: homo sapiens

<400> SEQUENCE: 1

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 2
<211> LENGTH: 326
<212> TYPE: PRT
<213> ORGANISM: homo sapiens

<400> SEQUENCE: 2

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Pro Val Ala Gly Pro Ser Val Phe Leu Phe Pro Pro Lys Pro Lys Asp
            115                 120                 125

Thr Leu Met Ile Ser Arg Thr Pro Glu Val Thr Cys Val Val Val Asp
130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
        195                 200                 205

Ala Pro Ile Glu Lys Thr Ile Ser Lys Thr Lys Gly Gln Pro Arg Glu
    210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
            275                 280                 285

Leu Thr Val Asp Lys Ser Arg Trp Gln Gln Gly Asn Val Phe Ser Cys
        290                 295                 300

Ser Val Met His Glu Ala Leu His Asn His Tyr Thr Gln Lys Ser Leu
305                 310                 315                 320

Ser Leu Ser Pro Gly Lys
            325

<210> SEQ ID NO 3
<211> LENGTH: 377
<212> TYPE: PRT
<213> ORGANISM: homo sapiens

<400> SEQUENCE: 3

Ala Ser Thr Lys Gly Pro Ser Val Phe Pro Leu Ala Pro Cys Ser Arg
1               5                   10                  15

Ser Thr Ser Gly Gly Thr Ala Ala Leu Gly Cys Leu Val Lys Asp Tyr
            20                  25                  30

```
Phe Pro Glu Pro Val Thr Val Ser Trp Asn Ser Gly Ala Leu Thr Ser
             35                  40                  45

Gly Val His Thr Phe Pro Ala Val Leu Gln Ser Ser Gly Leu Tyr Ser
 50                  55                  60

Leu Ser Ser Val Val Thr Val Pro Ser Ser Ser Leu Gly Thr Gln Thr
 65                  70                  75                  80

Tyr Thr Cys Asn Val Asn His Lys Pro Ser Asn Thr Lys Val Asp Lys
                 85                  90                  95

Arg Val Glu Leu Lys Thr Pro Leu Gly Asp Thr Thr His Thr Cys Pro
            100                 105                 110

Arg Cys Pro Glu Pro Lys Ser Cys Asp Thr Pro Pro Cys Pro Arg
            115                 120                 125

Cys Pro Glu Pro Lys Ser Cys Asp Thr Pro Pro Cys Pro Arg Cys
        130                 135                 140

Pro Glu Pro Lys Ser Cys Asp Thr Pro Pro Cys Pro Arg Cys Pro
145                 150                 155                 160

Ala Pro Glu Leu Leu Gly Gly Pro Ser Val Phe Leu Phe Pro Pro Lys
                165                 170                 175

Pro Lys Asp Thr Leu Met Ile Ser Arg Thr Pro Glu Val Thr Cys Val
            180                 185                 190

Val Val Asp Val Ser His Glu Asp Pro Glu Val Gln Phe Lys Trp Tyr
        195                 200                 205

Val Asp Gly Val Glu Val His Asn Ala Lys Thr Lys Pro Arg Glu Glu
210                 215                 220

Gln Tyr Asn Ser Thr Phe Arg Val Val Ser Val Leu Thr Val Leu His
225                 230                 235                 240

Gln Asp Trp Leu Asn Gly Lys Glu Tyr Lys Cys Lys Val Ser Asn Lys
                245                 250                 255

Ala Leu Pro Ala Pro Ile Glu Lys Thr Ile Ser Lys Thr Lys Gly Gln
            260                 265                 270

Pro Arg Glu Pro Gln Val Tyr Thr Leu Pro Pro Ser Arg Glu Glu Met
        275                 280                 285

Thr Lys Asn Gln Val Ser Leu Thr Cys Leu Val Lys Gly Phe Tyr Pro
    290                 295                 300

Ser Asp Ile Ala Val Glu Trp Glu Ser Ser Gly Gln Pro Glu Asn Asn
305                 310                 315                 320

Tyr Asn Thr Thr Pro Pro Met Leu Asp Ser Asp Gly Ser Phe Phe Leu
                325                 330                 335

Tyr Ser Lys Leu Thr Val Asp Lys Ser Arg Trp Gln Gln Gly Asn Ile
            340                 345                 350

Phe Ser Cys Ser Val Met His Glu Ala Leu His Asn Arg Phe Thr Gln
        355                 360                 365

Lys Ser Leu Ser Leu Ser Pro Gly Lys
        370                 375

<210> SEQ ID NO 4
<211> LENGTH: 327
<212> TYPE: PRT
<213> ORGANISM: homo sapiens

<400> SEQUENCE: 4

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30
```

```
Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Lys Thr
 65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Ser Cys Pro Ala Pro
            100                 105                 110

Glu Phe Leu Gly Gly Pro Ser Val Phe Leu Phe Pro Pro Lys Pro Lys
            115                 120                 125

Asp Thr Leu Met Ile Ser Arg Thr Pro Glu Val Thr Cys Val Val Val
        130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Gln Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 5
<211> LENGTH: 330
<212> TYPE: PRT
<213> ORGANISM: homo sapiens

<400> SEQUENCE: 5

Ala Ser Thr Lys Gly Pro Ser Val Phe Pro Leu Ala Pro Ser Ser Lys
 1               5                  10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
```

-continued

```
                65                  70                  75                  80
Tyr Ile Cys Asn Val Asn His Lys Pro Ser Asn Thr Lys Val Asp Lys
                    85                  90                  95

Arg Val Glu Pro Lys Ser Cys Asp Lys Thr His Thr Cys Pro Pro Cys
                100                 105                 110

Pro Ala Pro Glu Leu Leu Gly Gly Pro Ser Val Phe Leu Phe Pro Pro
                115                 120                 125

Lys Pro Lys Asp Thr Leu Met Ile Ser Arg Thr Pro Glu Val Thr Cys
            130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 6
<211> LENGTH: 4
<212> TYPE: PRT
<213> ORGANISM: homo sapiens

<400> SEQUENCE: 6

Pro Gly Lys Pro
1

<210> SEQ ID NO 7
<211> LENGTH: 5
<212> TYPE: PRT
<213> ORGANISM: homo sapiens
```

```
<400> SEQUENCE: 7

Pro Gly Lys Lys Pro
1               5

<210> SEQ ID NO 8
<211> LENGTH: 6
<212> TYPE: PRT
<213> ORGANISM: homo sapiens

<400> SEQUENCE: 8

Pro Gly Lys Lys Lys Pro
1               5
```

MODULATION OF COMPLEMENT-DEPENDENT CYTOTOXICITY THROUGH MODIFICATIONS OF THE C-TERMINUS OF ANTIBODY HEAVY CHAINS

RELATED APPLICATIONS

This application is a divisional of U.S. patent application Ser. No. 14/130,580, filed on Apr. 21, 2014, which is a 35 U.S.C. 371 national stage filing of PCT/EP2012/063338, filed on Jul. 6, 2012, which claims the benefit of U.S. Provisional Application No. 61/504,987, filed on Jul. 6, 2011, and Danish Patent Application No. PA 2011 00518, filed on Jul. 6, 2011. The contents of the aforementioned applications are hereby incorporated by reference.

SEQUENCE LISTING

The instant application contains a Sequence Listing which has been submitted electronically in ASCII format and is hereby incorporated by reference in its entirety. Said ASCII copy, created on Apr. 30, 2019, is named GMI_136USDV_Sequence_Listing.txt and is 15,579 bytes in size.

RELATED APPLICATIONS

This application is a divisional of U.S. patent application Ser. No. 14/130,580, filed on Apr. 21, 2014 (now U.S. Pat. No. 10,323,081), which is a 35 U.S.C. 371 national stage filing of PCT/EP2012/063338, filed on Jul. 6, 2012, which claims the benefit of U.S. Provisional Application No. 61/504,987, filed on Jul. 6, 2011, and Danish Patent Application No. PA 2011 00518, filed on Jul. 6, 2011. The contents of the aforementioned applications are hereby incorporated by reference.

SEQUENCE LISTING

The instant application contains a Sequence Listing which has been submitted electronically in ASCII format and is hereby incorporated by reference in its entirety. Said ASCII copy, created on Apr. 30, 2019, is named GMI_136USDV_Sequence_Listing.txt and is 15,579 bytes in size.

FIELD OF THE INVENTION

The present invention relates to antibodies and their ability to induce complement-dependent cytotoxicity (CDC). Antibody variants are provided that have altered ability to mediate CDC due to modifications at the C-terminus of their heavy chains. Furthermore, the invention provides methods of generating such antibodies, and nucleotide constructs and host cells suitable for the production of said antibodies.

BACKGROUND OF THE INVENTION

Monoclonal antibodies have in recent years become successful therapeutic molecules, in particular for the treatment of cancer and autoimmune diseases. Effector functions mediated by the Fc region of antibodies, such as antibody-dependent cell-mediated cytotoxicity (ADCC) and complement-dependent cytotoxicity (CDC) are often important mechanisms for the clinical efficacy of monoclonal antibodies.

Antibody-induced CDC is mediated through the proteins of the classical complement cascade. This cascade is triggered by binding of the complement protein C1q to the antibody. C1q is composed of a bundle of six heterotrimeric subunits having globular heads and collagen-like tails. Binding of C1q to the Fc region of an antibody is known to involve the CH2 region of the antibody (Duncan and Winter (1988) Nature 332:738). Furthermore, sugar moieties on the Fc region are known to influence the binding of C1q (Raju (2008) Curr Opin Immunol 20:471).

Monoclonal antibodies are complex molecules that can undergo many types of enzymatic and non-enzymatic post-translational modifications, including formation of disulfide bonds, glycosylation, glycation, N-terminal glutamine cyclization, C-terminal lysine processing (removal), deamidation, isomerization, oxidation and peptide bond cleavage (for a review of these modifications, see by Liu et al. (2008) J Pharm Sci 97: 2426).

Removal of C-terminal lysines by carboxypeptidases from the heavy chain is a commonly observed antibody modification, both upon recombinant expression of antibodies in mammalian cells, as well as in vivo in human serum (Cai et al. (2010) Biotechnol. Bioeng. September 9). Removal is often partial, resulting in a mixed population of antibodies with zero (K0), one (K1) or two (K2) C-terminal lysines (i.e., in the case of K2, one C-terminal lysine in each heavy chain of the antibody). In particular, B cell hybridomas produce mixtures of K0, K1 and K2 molecules (Dick et al. (2008) Biotech. Bioeng. 100:1132).

WO 2009027471 describes that deletion of the codon for the C-terminal lysine of a heavy chain of an antibody can result in higher antibody titers upon expression in Chinese Hamster Ovary (CHO) cells.

WO 2008006554 describes that an antibody preparation produced in Δxyl-t/Δfuc-t moss cells comprises an N-glycan structure free of fucose and xylose and lacks C-terminal lysine residues. The ability of this preparation to mediate ADCC was less inhibited by serum than a preparation of the same antibody produced in murine Sp2/0 cells. Complement-mediated lytic activity, on the other hand, was reduced. Removal of the C-terminal lysine residue was proposed to increase ADCC, although the effect of this modification alone was not tested.

The general belief in the art has been that C-terminal lysines have little or no effect on antibody function, see e.g. the literature review by Cai et al. (2010) supra, which concluded that no activity had been attributed to C-terminal lysines, or Harris (2005) Dev Biol (Basel) 122:127 which stated that the presence or absence of heavy chain Lys residues had no effect on antigen binding, and was not likely to influence Fc effector functions, clearance or any other biological property.

Antes et al. (2007) J Chromatogr. B 852:250 described testing the effect of C-terminal lysines on CDC. Antibody preparations were generated in Sp2/0 cells containing a significant subpopulation of C-terminal lysine-containing antibody molecules. Proteolytic removal of the C-terminal lysines had no effect on the ability of these antibody preparations to mediate CDC. The authors concluded, e.g., that both antibody variants—clipped and unclipped—elicited the same potency in a complement dependent cytotoxicity (CDC) assay demonstrating that lysine clipping of IGN311 does not impair Fc-mediated effector functions.

SUMMARY OF THE INVENTION

It has now surprisingly been found that lysines and other charged amino acid residues at the C-terminus of the heavy chains of an antibody do in fact have a major impact on their ability to mediate CDC.

Without being bound by any specific theory, it is hypothesized that this was not detected previously, because pure preparations of the K0, K1 and K2 forms were not compared.

The observation, described in the Examples herein, of the relationship between the presence of C-terminal charged residues and potency to mediate CDC provides the basis for novel antibody products having altered CDC properties as well as novel antibody production methods.

In a first aspect, the present invention provides a method for producing an antibody in a host cell, such as an antibody having increased CDC, wherein said antibody comprises at least a heavy chain, said method comprising the following steps:

a) providing a nucleotide construct encoding said heavy chain, wherein said construct does not encode a lysine residue at the C-terminus of said heavy chain, b) expressing said nucleotide construct in a host cell, with the proviso that said host cell is not a CHO cell or a moss cell, and c) recovering said antibody from a cell culture of said host cell.

In another aspect, the invention relates to a method for increasing the ability of an antibody to mediate CDC, said method comprising the step of removing a C-terminal lysine residue from the heavy chains of an antibody.

The product of the above methods is a population of antibody molecules having an increased ability to mediate CDC as compared to corresponding antibody molecules containing a C-terminal lysine residue. Such antibodies are useful for a number of purposes, e.g. therapeutic purposes, where killing of target cells is desired. This may, for example, be desired in the treatment of cancer.

In a further aspect, the invention provides an antibody variant comprising a heavy chain comprising at least one charged amino acid residue in the C-terminal region, wherein said charged amino acid residue is not susceptible to proteolytic removal.

This antibody variant has a decreased ability to mediate CDC as compared to a corresponding antibody molecule lacking one or both C-terminal lysine residues. Such antibodies are useful for applications, e.g. therapeutic applications, where only silencing of a target is desired. This can be advantageous in, e.g., the treatment of autoimmune diseases or inflammation.

In further aspects, the invention relates to methods, nucleotide constructs and host cells for producing antibody variants having at least one charged amino acid residue in the C-terminal region of the heavy chain, wherein said charged amino acid residue is not susceptible to proteolytic removal.

In a further aspect, the invention relates to a mammalian cell which has been genetically modified to eliminate the activity of carboxypeptidases capable of removing C-terminal lysines from heavy chains.

In even further aspects, the invention provides compositions of antibodies which have been modified to strengthen intermolecular interactions between antibody molecules in order to strengthen their ability to mediate effector functions, such as CDC. In one such aspect, the invention relates to an antibody mixture comprising a subpopulation of antibody variant molecules comprising heavy chains having at least one positively-charged amino acid residue in the C-terminal region and a subpopulation of antibody variant molecules comprising heavy chains having at least one negatively-charged amino acid residue in the C-terminal region, wherein said positively-charged and negatively-charged amino acid residues are not susceptible to proteolytic removal.

In another such aspect, the invention provides an antibody comprising a heavy chain having a variant C-terminal region, comprising one or more amino acid modifications that favour intermolecular C-terminal interactions between antibody molecules.

Figure 1A:
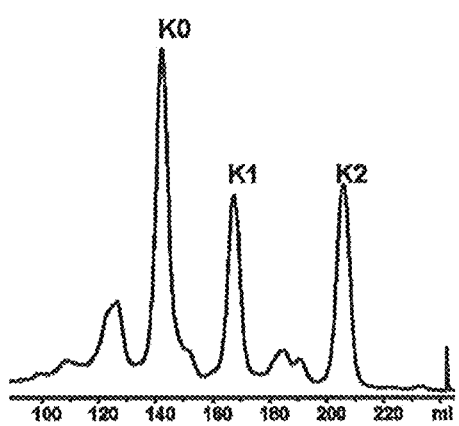
FIGS. 1A-1F: CIEX profiles, cIEF and SDS-PAGE analysis of C-terminal lysine isoforms of anti-CD20 and anti-CD38 antibodies.
Figure 1B:
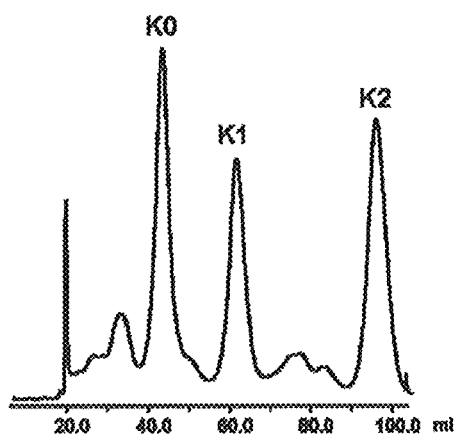
Figure 1C:
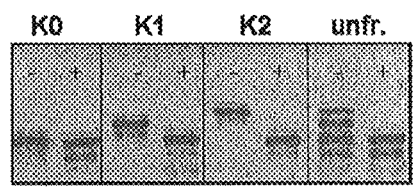
Figure 1D:
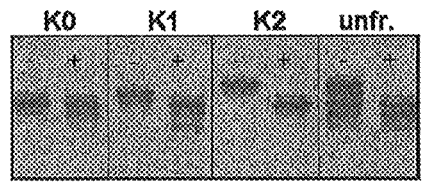
Figure 1E:
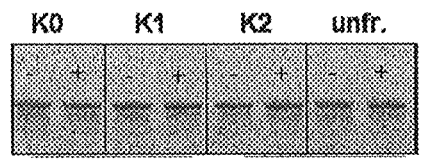
Figure 1F:
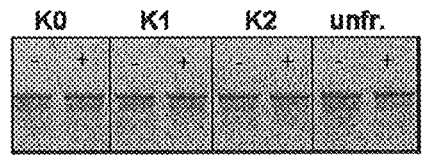

CIEX profiles of anti-CD20 (FIG. 1A) and anti-CD38 (FIG. 1B) antibodies. cIEF profiles of unfractionated antibody (unfr.), and collected isoforms, containing zero, one or two C-terminal lysines per IgG molecule (K0, K1, K2), of anti-CD20 (FIG. 1C) and anti-CD38 (FIG. 1D) antibodies. SDS PAGE analysis of unfractionated antibodies and collected isoforms of anti-CD20 (FIG. 1E) and anti-CD38 (FIG. 1F) antibodies. Samples were analyzed untreated (−) or after carboxypeptidase B treatment (+) (FIGS. 1C-1F).

Figure 2:
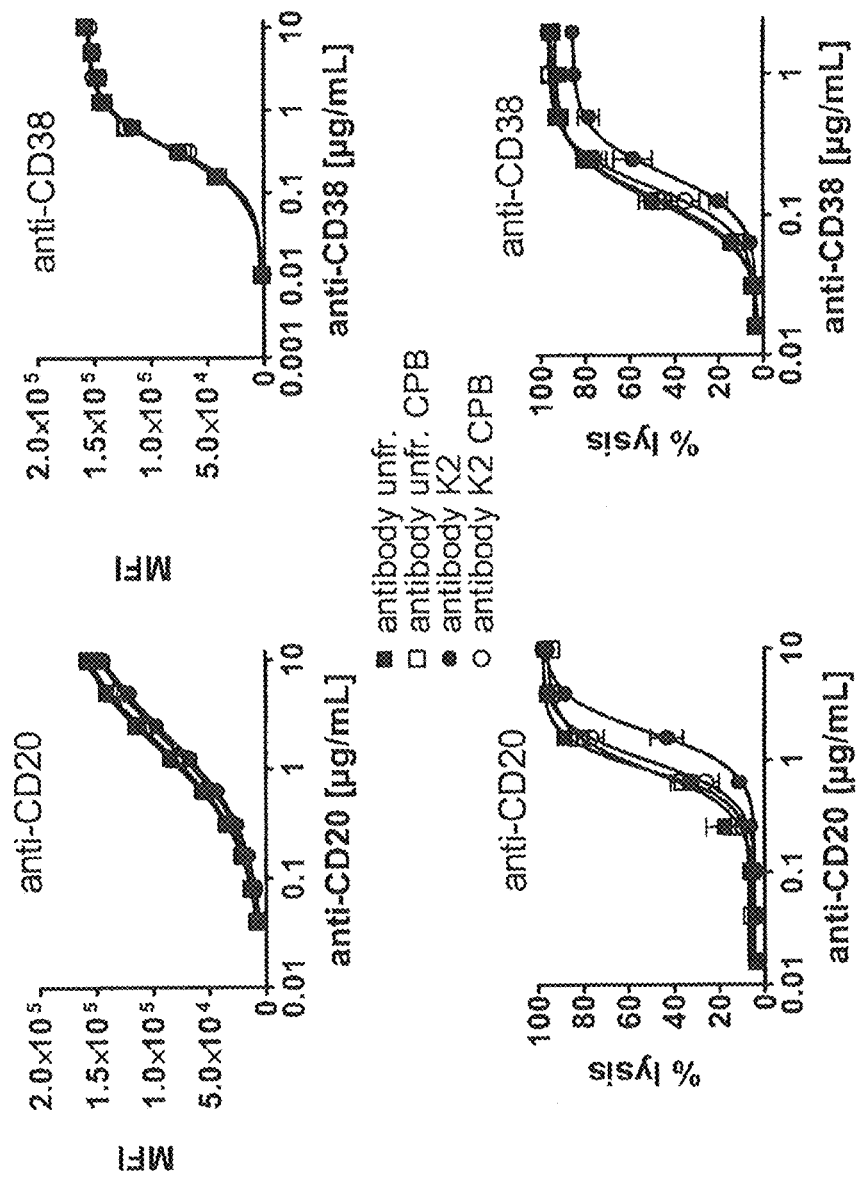

FIG. 2—Binding curves and CDC induction by C-terminal lysine isoforms of anti-CD20 and anti-CD38 antibodies.

Binding to Daudi cells of unfractionated antibodies (unfr.) and collected K2 isoforms of anti-CD20 and anti-CD38 antibodies with and without carboxypeptidase B (CPB) treatment, as determined by FACS analysis (upper panel). Data shown are mean fluorescence intensities (MFI). Induction of CDC of Daudi cells by unfractionated antibodies and collected K2 isoforms of anti-CD20 and anti-CD38 antibodies with and without carboxypeptidase B treatment, as measured using propidium iodide staining method (lower panel). Data shown are percentages lysis.

Figure 3:
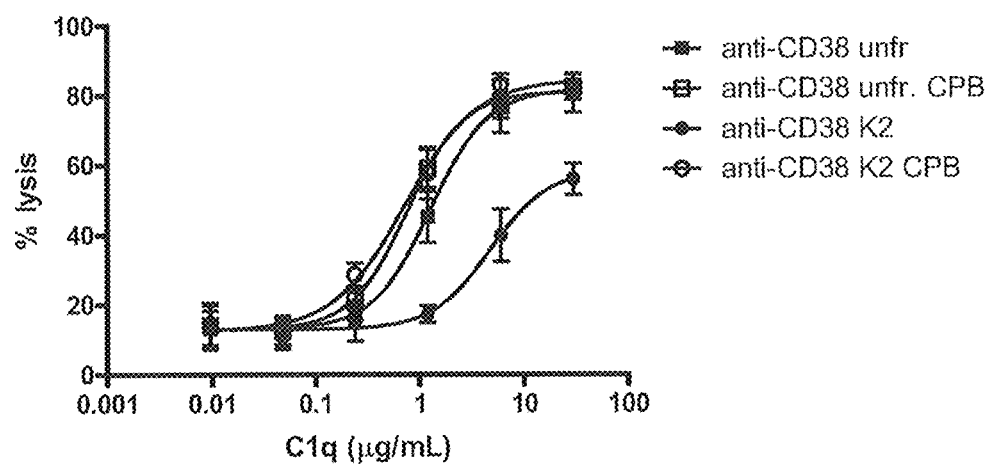

FIG. 3—Efficacy of C1q utilization by C-terminal lysine isoforms of anti-CD38 antibody.

Induction of CDC of Daudi cells by unfractionated and collected K2 isoform of anti-CD38 antibody with and without carboxypeptidase B (CPB) treatment, as measured using propidium iodide staining method. Cells were incubated with a fixed antibody concentration (10 µg/mL). Titrated amounts of C1q were added in the assay as complement source. Data shown are mean percentages of lysis±S.E.M of three experiments.

Figure 4A:
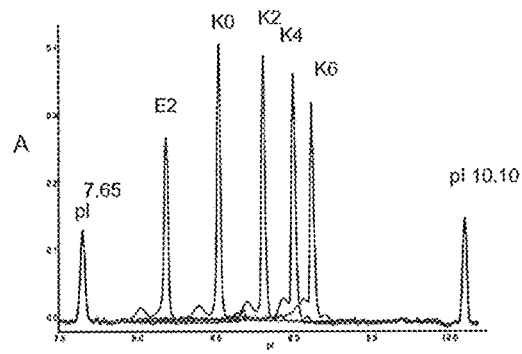
Figure 4B:
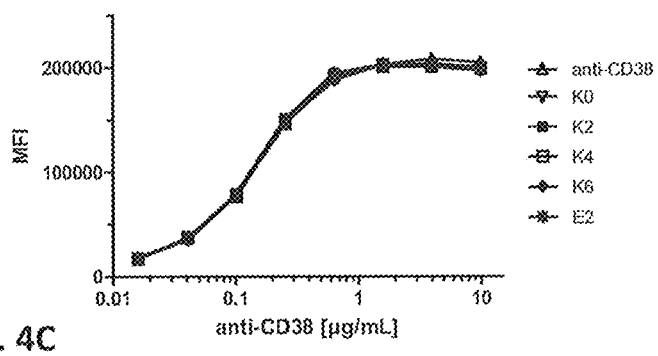
Figure 4C:
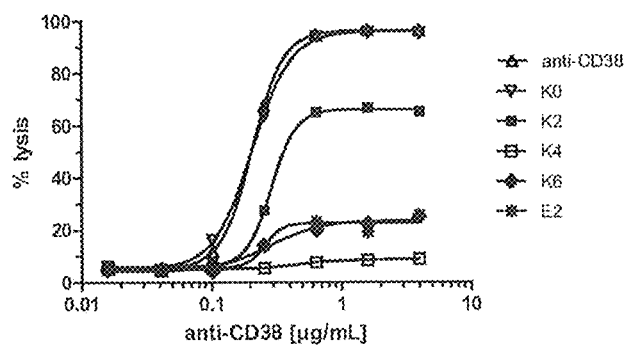

FIGS. 4A-4C—cIEF analysis, binding and CDC induction by anti-CD38 antibody and mutants.

cIEF analysis of anti-CD38 antibody and mutants (FIG. 4A). Binding of anti-CD38 antibody and mutants to Daudi cells as analyzed by FACS analysis (FIG. 4B). Data shown are mean fluorescence intensities (MFI). Induction of CDC of Daudi cells by anti-CD38 antibody and mutants as measured by PI staining method (FIG. 4C). Data shown are percentages lysis.

FIGS. 5A-5D—CDC induction by mixtures of anti-CD38 antibody mutants.

K0 and K4 (FIG. 5A) or K0 and E2 (FIG. 5B) mutants were mixed in different ratios, as indicated, and induction of CDC of Daudi cells was measured by propidium iodide staining method. Total IgG concentration was 10 µg/mL. Induction of CDC by K4 mutant, E2 mutant or a 1:1 mixture of both (FIG. 5C). Total IgG concentration was titrated from 10 µg/mL to 0.016 µg/mL. K0 is shown as positive control. Induction of CDC by E2:K4 mutant mixtures in different ratios, at two total IgG concentrations (10 µg/mL and 0.25 µg/mL) (FIG. 5D). Data shown (FIGS. 5A-5D) are percentages (maximal) lysis.

DETAILED DESCRIPTION OF THE INVENTION

Definitions

The term "immunoglobulin" refers to a class of structurally related glycoproteins consisting of two pairs of polypeptide chains, one pair of light (L) low molecular weight chains and one pair of heavy (H) chains, all four interconnected by disulfide bonds. The structure of immunoglobulins has been well characterized. See for instance Fundamental Immunology Ch. 7 (Paul, W., ed., 2nd ed. Raven Press, N.Y. (1989)). Briefly, each heavy chain typically is comprised of a heavy chain variable region (abbreviated herein as VH) and a heavy chain constant region. The heavy chain constant region typically is comprised of three domains, CH1, CH2, and CH3. The heavy chains are interconnected via disulfide bonds in the so-called "hinge region". Each light chain typically is comprised of a light chain variable region (abbreviated herein as VL) and a light chain constant region. The light chain constant region typically is comprised of one domain, CL. Typically, the numbering of amino acid residues in the constant region is performed according to the EU-index as described in Kabat et al., Sequences of Proteins of Immunological Interest, 5th Ed. Public Health Service, National Institutes of Health, Bethesda, Md. (1991). The VH and VL regions may be further subdivided into regions of hypervariability (or hypervariable regions which may be hypervariable in sequence and/or form of structurally defined loops), also termed complementarity determining regions (CDRs), interspersed with regions that are more conserved, termed framework regions (FRs). Each VH and VL is typically composed of three CDRs and four FRs, arranged from amino-terminus to carboxy-terminus in the following order: FR1, CDR1, FR2, CDR2, FR3, CDR3, FR4 (see also Chothia and Lesk J. Mol. Biol. 196, 901 917 (1987)).

The term "antibody" (Ab) in the context of the present invention refers to an immunoglobulin molecule, a fragment of an immunoglobulin molecule, or a derivative of either thereof, which has the ability to specifically bind to an antigen under typical physiological conditions with a half life of significant periods of time, such as at least about 30 minutes, at least about 45 minutes, at least about one hour, at least about two hours, at least about four hours, at least about eight hours, at least about 12 hours, about 24 hours or more, about 48 hours or more, about three, four, five, six, seven or more days, etc., or any other relevant functionally-defined period (such as a time sufficient to induce, promote, enhance, and/or modulate a physiological response associated with antibody binding to the antigen and/or time sufficient for the antibody to recruit an effector activity). The variable regions of the heavy and light chains of the immunoglobulin molecule contain a binding domain that interacts with an antigen. The constant regions of the antibodies may mediate the binding of the immunoglobulin to host tissues or factors, including various cells of the immune system (such as effector cells) and components of the complement system such as C1q, the first component in the classical pathway of complement activation. An antibody may also be a bispecific antibody, diabody or similar molecule. The term "bispecific antibody" refers to antibody having specificities for at least two different, typically non-overlapping, epitopes. As indicated above, the term antibody herein, unless otherwise stated or clearly contradicted by the context, includes fragments of an antibody that retain the ability to specifically bind to the antigen. Such fragments may be provided by any known technique, such as enzymatic cleavage, peptide synthesis and recombinant expression techniques. It has been shown that the antigen-binding function of an antibody may be performed by fragments of a full-length antibody. It also should be understood that the term antibody, unless specified otherwise, also includes polyclonal antibodies, monoclonal antibodies and antibody-like polypeptides, such as chimeric antibodies and humanized antibodies. An antibody as generated can possess any isotype. In one embodiment of the invention, the antibody is isolated and/or purified.

As used herein, "isotype" refers to the immunoglobulin class (for instance IgG1, IgG2, IgG3, IgG4, IgD, IgA, IgE, or IgM) that is encoded by heavy chain constant region genes.

Unless stated otherwise, the term "C-terminal lysine residue" refers to the lysine residue at the C-terminus of the heavy chain (i.e. the C-terminus of the CH3 region).

Unless stated otherwise, the term "C-terminal region", refers to the C-terminal region of the heavy chain of an antibody, consisting of the six most C-terminal amino acids of the heavy chain polypeptide.

The term "full-length antibody" when used herein, refers to an antibody which contains all heavy and light chain constant and variable domains that are normally found in an antibody of that isotype.

The term "human antibody", as used herein, is intended to include antibodies having variable and constant regions derived from human germline immunoglobulin sequences. The human antibodies of the invention may include amino acid residues not encoded by human germline immunoglobulin sequences (e.g., mutations introduced by random or site-specific mutagenesis in vitro or by somatic mutation in vivo). However, the term "human antibody", as used herein, is not intended to include antibodies in which CDR sequences derived from the germline of another mammalian species, such as a mouse, have been grafted onto human framework sequences.

When used herein, the term "heavy-chain antibody" refers to an antibody which consists only of two heavy chains and lacks the two light chains usually found in antibodies. Heavy-chain antibodies, which naturally occur in e.g. camelids, can bind antigens despite having only VH domains, see e.g. Hamers-Casterman (1993) Nature 363:446.

As used herein, the term "binding", in the context of the binding of an antibody to a predetermined antigen, typically is a binding with an affinity corresponding to a $K_D$ of about $10^{-6}$ M or less, e.g. $10^{-7}$ M or less, such as about $10^{-8}$ M or less, such as about $10^{-9}$ M or less, about $10^{-10}$ M or less, or about $10^{-11}$ M or even less, when determined by for instance surface plasmon resonance (SPR) technology in a BIAcore 3000 instrument, using the antigen as the ligand and the antibody as the analyte, and binds to the predetermined antigen with an affinity corresponding to a $K_D$ that is at least ten-fold lower, such as at least 100-fold lower, for instance at least 1,000-fold lower, such as at least 10,000-fold lower, for instance at least 100,000-fold lower than its affinity for binding to a non-specific antigen (e.g., BSA, casein), other than the predetermined antigen or a closely-related antigen. The amount with which the affinity is lower is dependent on the $K_D$ of the antibody, so that when the $K_D$ of the antibody is very low (that is, the antibody is highly specific), then the amount with which the affinity for the antigen is lower than the affinity for a non-specific antigen may be at least 10,000-fold. The term "$K_D$" (M), as used herein, refers to the dissociation equilibrium constant of a particular antibody-antigen interaction.

An "isolated antibody," as used herein, denotes that the material has been removed from its original environment (e.g., the natural environment if it is naturally occurring or the host cell if it is recombinantly expressed). It is also advantageous that the antibodies be in purified form. The term "purified" does not require absolute purity; rather, it is intended as a relative definition, indicating an increase of the antibody concentration relative to the concentration of contaminants in a composition as compared to the starting material.

The term "host cell", as used herein, is intended to refer to a cell into which a recombinant nucleotide construct or an expression vector has been introduced, e.g. a nucleotide construct or an expression vector encoding an antibody of the invention. Recombinant host cells include, for example, transfectomas, such as CHO cells, HEK293 cells, NS0 cells or lymphocytic cells, or plant cells, fungal cells, such as yeast cells or prokaryotic cells.

Further Aspects and Embodiments of the Invention

As described above, in a first aspect, the invention relates to methods for increasing the ability of an antibody to mediate CDC by reducing the number of charged amino acid residues in the C-terminal region of the heavy chain. Antibody products having increased ability to mediate CDC can be obtained by post-translational proteolytic removal of the charged residue from the heavy chain or by recombinant production of the antibody from a nucleotide construct lacking codons for charged amino acids, such as lysines, in the region encoding the C-terminus.

Thus, in a first aspect, the invention provides a method for producing an antibody in a host cell, wherein said antibody comprises at least a heavy chain, said method comprising the following steps:
a) providing a nucleotide construct encoding said heavy chain, wherein said construct does not encode a lysine residue at the C-terminus of said heavy chain,
b) expressing said nucleotide construct in a host cell, with the proviso that said host cell is not a CHO cell or a moss cell, and
c) recovering said antibody from a cell culture of said host cell.

Typically, the heavy chain comprises a constant region comprising at least a CH3 domain, at least a CH2 and a CH3 domain, or all of a CH1, a CH2 and a CH3 domain. In one embodiment, the heavy chain comprises at least a CH2 and a CH3 domain.

In some embodiments, the antibody is a heavy-chain antibody. In most embodiments, however, the antibody will also contain a light chain and thus said host cell further expresses a light-chain-encoding construct, either on the same or a different vector.

Host cells suitable for the recombinant expression of antibodies are well-known in the art. In a one embodiment, said host cell is a cell which is capable of Asn-linked glycosylation of proteins, e.g. a eukaryotic cell, such as a mammalian cell, e.g. a human cell. In a further embodiment, said host cell is a non-human cell which is genetically engineered to produce glycoproteins having human-like or human glycosylation. Examples of such cells are genetically-modified *Pichia pastoris* [Hamilton et al., Science 301 (2003) 1244-1246; Potgieter et al., J. Biotechnology 139 (2009) 318-325] and genetically-modified *Lemna minor* [Cox et al., Nature Biotechnology 12 (2006) 1591-1597].

In one embodiment, said host cell is not capable of efficiently removing C-terminal lysine residues from antibody heavy chains. For example, Table 2 in Liu et al. (2008) J Pharm Sci 97: 2426 (incorporated herein by reference) lists a number of such antibody production systems, e.g. Sp2/0, NS0 or transgenic mammary gland (goat), wherein only partial removal of C-terminal lysines is obtained.

More specifically, such a host cell may be a cell which, when expressing a C-terminal lysine-containing construct, would produce an antibody preparation wherein more than 10% of the antibody molecules is in the K2 isoform, e.g. wherein more the 30% is in the K2 isoform. Table 1 gives expected amounts of K0, K1 and K2 as a function of C-terminal cleavage. Thus, phrased in another manner, a preferred host cell is a host cell in which more than 30% of the heavy chains remain uncleaved at the C-terminus, e.g. wherein more than 60% of the heavy chains remain uncleaved at the C-terminus of the heavy chain.

TABLE 1

| % uncleaved | % K0 in batch | % K1 in batch | % K2 in batch |
| --- | --- | --- | --- |
| 10 | 81 | 18 | 1 |
| 20 | 64 | 32 | 4 |
| 30 | 49 | 42 | 9 |
| 40 | 36 | 48 | 16 |
| 50 | 25 | 50 | 25 |
| 60 | 16 | 48 | 36 |
| 70 | 9 | 42 | 49 |
| 80 | 4 | 32 | 64 |
| 90 | 1 | 18 | 81 |
| 100 | 0 | 0 | 100 |

In a further embodiment of the invention, said host cell is selected from the group consisting of:
(i) a yeast cell, e.g. a *Pichia pastoris* or *Saccharomyces cerevisiae, Hansenula polymorpha* and *Ogataea minuta* and
(ii) a filamentous fungal cell, such as *Aspergillus awamori, Aspergillus niger, Aspergillus oryzea, Trichoderma reesi* and
(iii) a plant cell, such as an *Arabidopsis* cell, Lemna minor, *Nicotiana benthamiana* (tobacco), oilseed crop plant (*Brassica napus*), soybean, rice, maize (*Zea mays*) or carrot cells, and
(iv) an NS0, Sp2/0 or PER.C6 cell.

Recombinant production of antibodies in yeasts and filamentous fungi has e.g. been described and reviewed by Joosten et al. (2003) Microbial Cell Factories 2:1 and Gasser and Mattanovich (2007) Biotech Lett 29:201. For production of antibodies in plant cells, see e.g. Cox et al. (2006) Nat Biotechnol 24:1591, Decker and Reski (2007) Curr Opin Biotechnol 18:393, Giritch et al. (2006) Proc Natl Acad Sc USA 103:14701 or Hood et al. (2002) Curr Opin Biotechnol 13:630. Antibody expression in NS0 cell lines has, for example, been described by Dempsey et al. (2003) Biotechnol. Prog. 19:175. Jones et al. (2003) Biotechnol Prog 19:163, inter alia, have described antibody production in human PER.C6 cells. For antibody production in Sp2/0 cells, see e.g. Yang et al. (2007) Biotechnol Bioeng. 98:141.

In a further embodiment, wherein said heavy-chain-encoding construct does not encode a lysine or an arginine at the C-terminus of said heavy chain, preferably said heavychain-encoding construct does not encode a charged amino acid residue at the C-terminus of said heavy chain. More preferably, said heavy-chain-encoding construct does not contain any codon for a charged amino acid residue among the codon coding for the six most C-terminal amino acids.

In one embodiment, the antibody is a human antibody comprising a human heavy chain. The antibody can be of any isotype, including, but not limited to, IgG1, IgG2, IgG3, IgG4, IgD, IgA, IgE, and IgM. In one embodiment, the antibody is of an IgG isotype, such as an isotype selected from IgG1, IgG2, IgG3, and optionally IgG4. Specific wild-type heavy-chain constant sequences are provided below in SEQ ID NOS:1-5. However, different allotypes of each isotype are known in the art, and are described in Jefferies and Lefranc (2009), mAbs 1:4, 1-7, hereby incorporated by reference in its entirety.

In a further embodiment of the above method of the invention, the nucleotide construct provided in step a) is derived from, or designed based on, an original heavy-chain sequence having a codon for a C-terminal lysine residue. For example, the original heavy-chain sequence may comprise a C-terminal sequence which is residues 325-330 of SEQ ID NOS:1 (IgG1m (az) allotype) or 5 (IgG1m(f) allotype), or residues 321 to 326 of SEQ ID NO:4, as set forth below. Thus, said nucleotide construct may comprise a deletion or a substitution of the codon for the C-terminal lysine (k) residue compared to said original heavy-chain sequence. Accordingly, in one embodiment, the nucleotide construct comprises a C-terminal sequence which comprises or consists of residues 325-329 of SEQ ID NOS:1 or 5. In one embodiment, the nucleotide construct comprises a C-terminal sequence which comprises or consists of residues 321 to 325 of SEQ ID NO:4.

In one embodiment, said nucleotide construct encodes a heavy chain comprising a constant region sequence which, other than the C-terminal modification, comprises at least a CH3 domain, at least CH2 and CH3 domains, or CH1, CH2 and CH3 domains of the IgG1 isotype, optionally the IgG1m (f) allotype. In one embodiment, said nucleotide construct encodes a heavy chain comprising a constant region sequence which comprises at least a CH3 domain, at least CH2 and CH3 domains, or CH1, CH2 and CH3 domains of the IgG2 isotype, other than the C-terminal modification. In one embodiment, said nucleotide construct encodes a heavy chain comprising a constant region sequence which comprises at least a CH3 domain, at least CH2 and CH3 domains, or CH1, CH2 and CH3 domains of the IgG3 isotype, other than the C-terminal modification. In one embodiment, said nucleotide construct encodes a heavy chain comprising a constant region sequence which comprises at least a CH3 domain, at least CH2 and CH3 domains, or CH1, CH2 and CH3 domains of the IgG4 isotype, other than the C-terminal modification. In one embodiment, the heavy chain comprises a sequence selected from SEQ ID NOS:1-5, apart from the C-terminal lysine residue.

In an even further embodiment, said nucleotide construct, other than the C-terminal modification, encodes a heavy chain of the IgG1 or IgG2 isotype, i.e. has a constant region sequence which is identical in sequence to the IgG1 or IgG2 constant region, except for the C-terminal modification. In one embodiment, said nucleotide construct, other than the C-terminal modification, encodes a heavy chain of the IgG1 or IgG3 isotype, i.e. has a constant region sequence which is identical in sequence to the IgG1 or IgG3 constant region, except for the C-terminal modification. In a further embodiment, the C-terminal codon of said nucleotide construct encodes a Pro or a Gly residue, e.g. the -Pro-Gly-Lys sequence at the C-terminus of an IgG1 or IgG2 heavy chain would be truncated to -Pro-Gly or -Pro only.

In a further aspect, the invention relates to an antibody obtained or obtainable by the method of the invention described above.

In a yet further aspect, the invention relates to a host cell which is not capable of efficiently removing C-terminal lysine residues from antibody heavy chains, said host cell comprising a nucleotide construct encoding a heavy chain lacking a C-terminal lysine. Preferably, said host cell is not moss or CHO. More preferably, said host cell is of one of the types specified above under (i) to (iv).

In an even further aspect, the invention relates to a method for increasing the ability of an antibody to mediate CDC, said method comprising the step of removing a C-terminal lysine residue from the heavy chains of an antibody. In a preferred embodiment, the lysine residue is removed by enzymatic cleavage, e.g. using a carboxypeptidase, such as carboxypeptidase B or carboxypeptidase N (Cia et al. (2010) Supra). In one embodiment, said antibody is purified prior to removal of the C-terminal lysine residue.

As mentioned above, some cell types, e.g. hybridomas, produce heterogenous populations of antibody molecules, wherein some molecules contain one or two C-terminal lysines and others do not. As it is clear from the present work that C-terminal lysines affect the ability of antibodies to mediate CDC, such C-terminal heterogeneity may be undesired if different antibodies from a plurality of samples are to be compared, as there may be differences between different hybridomas with respect to the degree of C-terminal processing. To eliminate such differences, it may be advantageous to remove the C-terminal lysines from antibody samples prior to comparative testing in order to be able to better compare properties related to the binding properties of the antibodies.

Accordingly, in a further aspect, the invention relates to a method for testing a plurality of antibody-producing cell cultures, e.g. hybridoma cell cultures, for a desired property, said method comprising treating samples of said cultures to remove the C-terminal lysines as described above and testing the treated samples for the desired property. In some embodiments, it may be advantageous to remove cells and/or purify antibody from the culture sample before removal of the C-terminal lysines. In a preferred embodiment, the desired property to be tested is cell lysis or cell killing.

As explained above, in a further aspect, the invention relates to an antibody variant comprising a heavy chain having at least one charged amino acid residue in the C-terminal region, such as one, two, three, four or more charged amino acids, wherein said charged amino acid residue is not susceptible to proteolytic removal.

Examples of charged amino acids residues include those having a positive charge, such as lysine (K or Lys), arginine (R or Arg) and histidine (H or His), and those having a negative charge, such as glutamic acid (E or Glu) and aspartic acid (D or Asp). In one embodiment, the charged amino acid residue is selected from lysine, arginine and histidine, such as from lysine and arginine, such as lysine. In one embodiment, the charged amino acid residue is selected from glutamic acid and aspartic acid, such as glutamine.

Such variants typically have reduced ability to mediate CDC as compared to a corresponding antibody lacking the charged residue. Such variants may e.g. be useful for therapeutic uses wherein reduced CDC is desired, e.g. uses wherein silencing of a target antigen, without killing of the target cell, is desired.

In some embodiments, the antibody is a heavy-chain antibody. In most embodiments, however, the antibody will further comprise a light chain.

In a one embodiment, said charged amino acid residue is not susceptible to removal by proteases of mammalian origin, preferably not susceptible to removal by proteases of CHO, HEK-293, PER.C6, NS0 or Sp2/0 origin, more preferably not susceptible to removal by proteases, such as carboxypeptidases, active in the secretory pathway of CHO, HEK-293, PER.C6, NS0 or Sp2/0 cells.

In a further embodiment, said charged amino acid residue is not susceptible to removal by human proteases, preferably not susceptible to removal by human proteases that can act on proteins in circulation, e.g. in blood.

In one embodiment, said charged amino acid is amongst the six most C-terminal amino acid residues, e.g. amongst the five most C-terminal amino acid residues of said heavy chain, such as amongst the four most C-terminal amino acid residues of said heavy chain, e.g. amongst the three most C-terminal amino acid residues of said heavy chain, such as amongst the two most C-terminal amino acid residues of said heavy chain, e.g. wherein said charged amino acid is the most C-terminal amino acid residue of said heavy chain.

In a further embodiment, said heavy chain comprises the CH3 sequence set forth in SEQ ID NO:1, 2, 3, 4 or 5 herein below, modified such that said charged amino acid is situated amongst the most six most C-terminal amino acid residues, i.e. from position 325 to 330, from position 321 to 326, from position 372 to 377, from 321 to 326 or from position 325 to 330, respectively.

```
SEQ ID NO: 1: The amino acid sequence of the IgG1 constant region
(accession number P01857; IgGm(za) allotype) (the CH3 sequence is
underlined)
    1    astkgpsvfp lapsskstsg gtaalgclvk dyfpepvtvs wnsgaltsgv 51    htfpavlqss glyslssvvt vpssslgtqt yicnvnhkps ntkvdkkvep 101    kscdkthtcp pcpapellgg psvflfppkp kdtlmisrtp evtcvvvdvs 151    hedpevkfnw yvdgvevhna ktkpreeqyn styrvvsvlt vlhqdwlngk 201    eykckvsnka lpapiektis kakgqprepq vytlppsrde ltknqvsltc 251    lvkgfypsdi avewesnqqp ennykttppv ldsdgsffly skltvdksrw 301    qqgnvfscsv mhealhnhyt qkslslspgk SEQ ID NO: 2: The amino acid sequence of the IgG2 constant region
(accession number P01859) (the CH3 sequence is underlined)
    1    astkgpsvfp lapcsrstse staalgclvk dyfpepvtvs wnsgaltsgv 51    htfpavlqss glyslssvvt vpssnfgtqt ytcnvdhkps ntkvdktver 101    kccvecppcp appvagpsvf lfppkpkdtl misrtpevtc vvvdvshedp 151    evqfnwyvdg vevhnaktkp reeqfnstfr vvsvltvvhq dwlngkeykc 201    kvsnkglpap iektisktkg qprepqvytl ppsreemtkn qvsltclvkg 251    fypsdiavew esnggpenny kttppmldsd gsfflysklt vdksrwqqgn 301    vfscsvmhea lhnhytqksl slspgk SEQ ID NO: 3: The amino acid sequence of the IgG3 constant region
(accession number P1860) (the CH3 sequence is underlined)
    1    astkgpsvfp lapcsrstsg gtaalgclvk dyfpepvtvs wnsgaltsgv 51    htfpavlqss glyslssvvt vpssslgtqt ytcnvnhkps ntkvdkrvel 101    ktplgdttht cprcpepksc dtppcprcp epkscdtppp cprcpepksc 151    dtpppcprcp apellggpsv flfppkpkdt lmisrtpevt cvvvdvshed 201    pevqfkwyvd gvevhnaktk preeqynstf rvvsvltvlh qdwlngkeyk 251    ckvsnkalpa piektisktk gqprepqvyt lppsreemtk nqvsltclvk 301    gfypsdiave wessgqpenn ynttppmlds dgsfflyskl tvdksrwqqg 351    nifscsvmhe alhnrftqks lslspgk SEQ ID NO: 4: The amino acid sequence of the IgG4 constant region (the
CH3 sequence is underlined)
astkgpsvfp lapcsrstse staalgclvk dyfpepvtvs wnsgaltsgv htfpavlqss glyslssvvt vpssslgtkt ytcnvdhkps ntkvdkrves kygppcpscp apeflggpsv flfppkpkdt lmisrtpevt cvvvdvsqed
```

-continued

```
pevqfnwyvd gvevhnaktk preeqfnsty rvvsvltvlh qdwlngkeyk ckvsnkglps siektiskak gqprepqvyt lppsqeemtk nqvsltclvk gfypsdiave wesngqpenn ykttppvlds dgsfflysrl tvdksrwqeg nvfscsvmhe alhnhytqks lslslqk
```

SEQ ID NO: 5: The amino acid sequence of the IgG1m(f) allotype constant
region (the CH3 sequence is underlined)

```
  1    astkgpsvfp lapsskstsg gtaalgclvk dyfpepvtvs wnsgaltsgv 51    htfpavlqss glyslssvvt vpssslgtqt yicnvnhkps ntkvdkrvep 101    kscdkthtcp pcpapellgg psvflfppkp kdtlmisrtp evtcvvvdvs 151    hedpevkfnw yvdgvevhna ktkpreeqyn styrvvsvlt vlhqdwlngk 201    eykckvsnka lpapiektis kakgqprepq vytlppsree mtknqvsltc 251    lvkgfypsdi avewesngqp ennykttppv ldsdgsffly skltvdksrw 301    qqgnvfscsv mhealhnhyt qkslslspgk
```

In a further embodiment, said heavy chain comprises the entire constant region sequence set forth in SEQ ID NO:1, 2, 3, 4 or 5 and said charged amino acid is situated amongst the six most C-terminal amino acid residues, i.e. from position 325 to 330, from position 321 to 326 or from position 372 to 377, respectively.

In one embodiment, said charged amino acid is a positively charged amino acid residue, preferably a lysine residue. As C-terminal lysines are normally susceptible to proteolytic removal, said variant will contain one or more amino acid modifications, such as additions or substitutions, at a position situated C-terminally of said lysine. For example, in one embodiment, said charged amino acid residue is not susceptible to proteolytic removal due to the presence of a proline residue situated C-terminally of said charged amino acid residue, wherein said proline residue is preferably placed immediately C-terminal of said charged amino acid residue, more preferably wherein said charged amino acid residue and said proline residue are the two most C-terminal amino acid residues of said heavy chain. For example, the antibody heavy chain may be an IgG1, IgG2, IgG3 or IgG4 heavy chain to which a proline residue has been added at the C-terminus.

In another embodiment, said charged amino acid is a negatively-charged amino acid residue, preferably a glutamic acid residue. Negatively-charged C-terminal residues are normally not susceptible to proteolytic removal upon expression in mammalian cells and thus, in some embodiments, such a variant does not contain further amino acid modifications.

In a further embodiment, said heavy chain comprises two or more charged amino acid residues in the C-terminal region, such as two, three, four or five charged amino acid residues, preferably having either all a positive charge or all a negative charge, optionally comprising further amino acid modifications C-terminally of said charged residues, e.g. a proline residue situated C-terminally of said charged residues.

In some embodiments, the specified amino acid modifications are the result of amino acid substitutions. In other embodiments, the specified amino acid modifications are the result of C-terminal amino acid additions.

In one embodiment, said heavy chain comprises a C-terminal sequence selected from pro-gly-glu (PGE), pro-gly-lys-pro (PGKP; SEQ ID NO:6), pro-gly-lys-lys-pro (PGKKP; SEQ ID NO:7), and pro-gly-lys-lys-lys-pro (PGKKKP; SEQ ID NO:8).

In one embodiment, said antibody is a human antibody, preferably a human IgG1 or a human IgG3 antibody.

In another embodiment, said antibody is not conjugated at the C-terminus, e.g. not conjugated to another molecule, such as a toxin or label. In a further embodiment, said antibody is not conjugated at the C-terminus, but is conjugated at another site of the molecule, e.g. the antibody may, at the other site, be linked to a compound selected from the group consisting of: a toxin (including a radioisotope) a prodrug or a drug. Such compounds may make killing of target cells more effective, e.g. in cancer therapy. The resulting antibody is thus an immunoconjugate.

In a further aspect, the invention relates to an antibody of the invention as described above for use as a medicament, in particular for use as a medicament for the treatment of diseases or disorders, wherein silencing (i.e. inhibition) of a target antigen is desired, without killing of the target cell. Examples of such diseases and disorders include autoimmune diseases and inflammation.

In a further aspect, the invention relates to a nucleotide construct encoding a heavy chain having a charged amino acid residue in the C-terminal region, wherein said charged amino acid residue is not susceptible to proteolytic removal. In a further embodiment, said nucleotide construct has any one or more of the further features described above for the antibody of the invention.

In a further aspect, the invention relates to a host cell capable of producing an antibody variant of the invention. Such a host cell may be a cell that has been transformed or transfected with a nucleotide construct of the invention or a host cell which has been genetically modified to eliminate the activity of carboxypeptidases capable of removing C-terminal lysines from heavy chains. Examples of host cells include CHO, HEK-293, PER.C6, NSO and Sp2/0.

In an even further aspect, the invention relates to a method for producing an antibody variant according to the invention comprising culturing a host cell according to the invention and recovering said antibody from the cell culture. In one embodiment, said host cell is a CHO or HEK cell comprising a nucleotide construct encoding a heavy chain with a negatively-charged amino acid residue at the C-terminus or a proline residue preceded by a positively-charged amino acid residue at the C-terminus.

In one aspect, the invention relates to a method for decreasing the ability of an antibody to mediate complement-dependent cytotoxicity, said method comprising the step of adding at least one charged amino acid residue, a proline residue, or both to the C-terminal region of the heavy-chains of an antibody. In one embodiment, a positively charged amino acid is inserted N-terminal to a proline residue already present in the C-terminal region. In one embodiment, a proline residue is added C-terminal to a lysine residue already present in the C-terminal region. In one embodiment, a positively charged amino acid and a proline is added to the C-terminal, wherein the positively charged amino acid is added N-terminal to the proline residue. In such embodiments, the positively charged amino acid can be selected from lysine, arginine and histidine, such as lysine or arginine, such as lysine.

In one embodiment, a positively charged amino acid is added to the C-terminal region. In such an embodiment, the positively charged amino acid can be selected from glutamic acid and aspartic acid.

In one embodiment, the method comprises adding one or more further charged amino acids to the C-terminal region.

As explained above, in a further aspect, the invention relates to an antibody mixture comprising a subpopulation of antibody variant molecules comprising heavy chains having a positively-charged amino acid residue in the C-terminal region and a subpopulation of antibody variant molecules comprising heavy chains having a negatively-charged amino acid residue C-terminal region, wherein said positively-charged and negatively-charged amino acid residues are not susceptible to proteolytic removal.

Without being bound any specific theory, it is hypothesized that electrostatic interactions between oppositely-charged residues reinforce intermolecular antibody interactions and thus facilitate the activation of the complement system.

In one embodiment, each of said subpopulations constitutes at least 10%, such as at least 20% of said mixture, e.g. at least 30% of said mixture.

In another embodiment, the antibody molecules within each of the two subpopulations comprise two identical heavy chains. In a further aspect, the invention relates to the antibody mixture according to the invention for use as a medicament, preferably for use in the treatment of cancer.

As explained above, in a further aspect, the invention relates to an antibody comprising a heavy chain having a variant C-terminal region, said variant C-terminal region comprising one or more amino acid modifications that favour intermolecular C-terminal interactions between antibody molecules. Without being bound by any specific theory, it is believed that strengthened intermolecular interactions between antibody molecules facilitate the activation of the complement system and thus result in an increased ability to mediate CDC compared to an antibody product lacking said amino acid modifications.

In one embodiment, said antibody comprises two non-identical heavy chains. In a particularly interesting embodiment hereof, one heavy chain of the antibody comprises a negatively-charged amino acid residue in the C-terminal region and the other heavy chain of the same antibody comprises a positively-charged charged amino acid residue in the C-terminal region, wherein said charged amino acid residues are not susceptible to proteolytic removal. Such an antibody will comprise a positively-charged heavy chain and a negatively-charged heavy chain and, thus, through alignment of oppositely-charged heavy chains between antibody molecules, form a multimeric complex containing strong intermolecular antibody-antibody interactions favoring CDC activation.

In one embodiment, such an antibody is a monospecific antibody. In another embodiment, it is a bispecific antibody.

In a further aspect, the invention relates to the above-described antibody of the invention for use as a medicament, preferably for use in the treatment of cancer.

In an even further aspect, the invention relates to a method for producing such an antibody comprising culturing a host cell comprising nucleotide constructs encoding said two different heavy chains and recovering said antibody from the cell culture of said host cell. Such a host cell may e.g. be a CHO or HEK cell.

As described above, the present invention inter alia relates to modifications of antibodies either to remove or add and/or protect charged amino acid residues at the C-terminus of the heavy chain. Antibodies to be used as starting material of the present invention before modification may e.g. be produced by the hybridoma method first described by Kohler et al., Nature 256, 495 (1975), or may be produced by recombinant DNA methods. Monoclonal antibodies may also be isolated from phage antibody libraries using the techniques described in, for example, Clackson et al., Nature 352, 624 628 (1991) and Marks et al., J. Mol. Biol. 222, 581 597 (1991). Monoclonal antibodies may be obtained from any suitable source. Thus, for example, monoclonal antibodies may be obtained from hybridomas prepared from murine splenic B cells obtained from mice immunized with an antigen of interest, for instance in the form of cells expressing the antigen on the surface, or a nucleic acid encoding an antigen of interest. Monoclonal antibodies may also be obtained from hybridomas derived from antibody-expressing cells of immunized humans or non-human mammals such as rats, dogs, primates, etc.

Antibodies to be used as starting material of the present invention may be e.g. chimeric or humanized antibodies. In another embodiment, the antibody is a human antibody. Human monoclonal antibodies may be generated using transgenic or transchromosomal mice, e.g. HuMAb Mice®, carrying parts of the human immune system rather than the mouse system. The HuMAb Mouse® contains a human immunoglobulin gene minilocus that encodes unrearranged human heavy (u and y) and k light chain immunoglobulin sequences, together with targeted mutations that inactivate the endogenous u and k chain loci (Lonberg, N. et al., Nature 368, 856 859 (1994)). Accordingly, the mice exhibit reduced expression of mouse IgM or k and in response to immunization, the introduced human heavy and light chain transgenes undergo class switching and somatic mutation to generate high affinity human IgG,κ monoclonal antibodies (Lonberg, N. et al. (1994), supra; reviewed in Lonberg, N. Handbook of Experimental Pharmacology 113, 49 101 (1994), Lonberg, N. and Huszar, D., Intern. Rev. Immunol. Vol. 13 65 93 (1995) and Harding, F. and Lonberg, N. Ann. N.Y. Acad. Sci 764 536 546 (1995)). The preparation of HuMAb Mice® is described in detail in Taylor, L. et al., Nucleic Acids Research 20, 6287 6295 (1992), Chen, J. et al., International Immunology 5, 647 656 (1993), Tuaillon et al., J. Immunol. 152, 2912 2920 (1994), Taylor, L. et al., International Immunology 6, 579 591 (1994), Fishwild, D. et al., Nature Biotechnology 14, 845 851 (1996). See also U.S. Pat. Nos. 5,545,806, 5,569,825, 5,625,126, 5,633,425, 5,789,650, 5,877,397, 5,661,016, 5,814,318, 5,874,299, 5,770,429, 5,545,807, WO 98/24884, WO 94/25585, WO 93/1227, WO 92/22645, WO 92/03918 and WO 01/09187.

Splenocytes from these transgenic mice may be used to generate hybridomas that secrete human monoclonal antibodies according to well known techniques.

Further, human antibodies of the present invention or antibodies of the present invention from other species may be identified through display-type technologies, including, without limitation, phage display, retroviral display, ribosomal display, mammalian display, and other techniques, using techniques well known in the art, and the resulting molecules may be subjected to additional maturation, such as affinity maturation, as such techniques are well known in the art.

Target Diseases and Antigens

Antibodies of the invention, lacking C-terminal lysine or other charged amino acid residues, may be used for many different purposes, such as purposes where increased cell killing via CDC is desired. Examples of suitable diseases include, without limitation, various forms of cancer. Examples of suitable antigen targets for such antibodies include, without limitation, tumor erbB1 (EGFR), erbB2 (HER2), erbB3, erbB4, MUC-1, CD4, CD19, CD20, CD25, CD32, CD37, CD38, CD74, CD138, CXCR5, c-Met, HERV-envelope protein, periostin, Bigh3, SPARC, BCR, CD79, EGFrvIII, IGFr, L1-CAM, AXL, Tissue Factor (TF), EpCAM and MRP3. Preferred antigens include CD20, HER2, EGFR, CD38, IGFR, CD25 and CD32. Exemplary antibodies include HuMAb 7D8, HuMAb 2F2 (described in WO2004035607) and HuMAb 005 (described in WO 2006099875).

Antibodies of the invention containing C-terminal lysine or other charged amino acid residues may, for example, be used in applications where CDC is not favored as a mode-of-action, e.g. in the treatment of autoimmune disease or inflammation. Examples of suitable antigen targets include, without limitation TNF-alpha, IL-1, VEGF, IL-6 and IL-8.

Compositions and Uses

In a further main aspect, the invention relates to a pharmaceutical composition comprising an antibody according to the invention as described herein and a pharmaceutically-acceptable carrier.

The pharmaceutical compositions may be formulated in accordance with conventional techniques such as those disclosed in Remington: The Science and Practice of Pharmacy, 19th Edition, Gennaro, Ed., Mack Publishing Co., Easton, Pa., 1995. A pharmaceutical composition of the present invention may e.g. include diluents, fillers, salts, buffers, detergents (e.g., a non-ionic detergent, such as Tween® 20 or Tween® 80), stabilizers (e.g., sugars or protein-free amino acids), preservatives, isotonicity agents, antioxidants, tissue fixatives, solubilizers, and/or other materials suitable for inclusion in a pharmaceutical composition. Examples of suitable aqueous and nonaqueous carriers which may be employed in the pharmaceutical compositions of the present invention include water, saline, phosphate-buffered saline, ethanol, dextrose, polyols (such as glycerol, propylene glycol, polyethylene glycol).

The pharmaceutical composition may be administered by any suitable route and mode. In one embodiment, a pharmaceutical composition of the present invention is administered parenterally. "Administered parenterally" as used herein means modes of administration other than enteral and topical administration, usually by injection, and include epidermal, intravenous, intramuscular, intra-arterial, intrathecal, intracapsular, intraorbital, intracardiac, intradermal, intraperitoneal, intratendinous, transtracheal, subcutaneous, subcuticular, intra-articular, subcapsular, subarachnoid, intraspinal, intracranial, intrathoracic, epidural and intrasternal injection and infusion.

The efficient dosages and the dosage regimens for the antibody depend on the disease or condition to be treated and may be determined by the persons skilled in the art. An exemplary, non-limiting range for a therapeutically effective amount of an antibody of the present invention is about 0.1-100 mg/kg, such as about 0.1-50 mg/kg, for example about 0.1-20 mg/kg, such as about 0.1-10 mg/kg, for instance about 0.5, about such as 0.3, about 1, about 3, about 5, or about 8 mg/kg.

Antibodies, of the present invention may also be administered in combination therapy, i.e., combined with other therapeutic agents relevant for the disease or condition to be treated. Accordingly, in one embodiment, the antibody-containing medicament is for combination with one or more further therapeutic agents, such as a cytotoxic, chemotherapeutic or anti-angiogenic agents. Such combined administration may be simultaneous, separate or sequential. In a further embodiment, the present invention provides a method for treating or preventing disease, such as cancer, which method comprises administration to a subject in need thereof of a therapeutically effective amount of an antibody of the present invention, in combination with radiotherapy and/or surgery.

EXAMPLES

Example 1: Cation Exchange Chromatography (CIEX) Profiles, Capillary Isoelectric Focusing (cIEF) and Sodium Dodecylsulphate Polyacrylamide Gel Electrophoresis (SDS-PAGE) Analysis of Anti-CD20 and Anti-CD38 C-terminal Lysine Variants Anti-CD20 antibody (2F2, described in WO 2004035607 (Genmab)) and anti-CD38 antibody (005, described in WO 2006099875 (Genmab)) were isolated from hybridoma supernatants and subjected to preparative cation exchange chromatography (CIEX). CIEX was performed on an AKTA Purifier system using a ProPac® WCX 10 (9 mm×250 mm) preparative column. Mobile phases A and B were 10 mM sodium phosphate (pH 7.2) and 25 mM sodium chloride in 10 mM sodium phosphate (pH 7.0). Antibodies were dialyzed O/N prior to injection. Linear gradients from 0% to 12% B in 60 min (anti-CD20) and from 8% to 13% B in 25 min (anti-CD38) were used. Flow rate was 4 mL/min for both antibody separations, and concentrations were determined by absorbance at 280 nm. For each antibody, six consecutive injections were performed and the individual K0, K1 and K2 isoforms (containing zero, one or two heavy-chain C-terminal lysines per antibody) were pooled, concentrated (Sartorius, Vivaspin®, 10,000 Da MWCO) and separation buffer was exchanged for PBS buffer. Pooled fractions were biochemically analyzed by cIEF and SDS PAGE without treatment or after carboxypeptidase B (CPB) treatment (500 μL [450 μg/mL] antibody in 20 mM sodium phosphate [pH 7.2] was mixed with 10 μL of 0.05 IU/μL CPB [Calbiochem] and incubated at 37° C. for 4 h). Samples were stored at −80° C. until further use. For CIEF analysis, antibody samples were diluted to 5 μg/mL and 20 μL was loaded onto a precast cIEF FocusGel 6-11 24S (ETC, Kirchentellinsfurt, Germany) with high pI Kit and pH 7.65 and 10.0 markers (Amersham, Piscataway, USA). Gels were pre-focused at 500 V, 30 mA and 10 W for 30 min, followed by focusing at 1500 V, 18 mA and 20 W for 90 min and 2000

V, 15 mA and 25 W for 30 min. Gels were fixed in 20% (w/v) trifluoroacetic acid at 30° C. for 45 min. Detection of the bands was performed using ammoniacal silver staining procedure recommended by the FocusGel supplier. cIEF gels were digitally imaged using the GeneGenius Imaging System (Synoptics, Cambridge, UK). All other reagents and devices used for cIEF were obtained from GE Healthcare (Uppsala, Sweden). Non-reduced SDS-PAGE was performed on 4-12% NuPAGE™ Bis-Tris SDS-PAGE gels (Invitrogen, Breda, The Netherlands). SDS-PAGE gels were digitally imaged using the GeneGenius Imaging System (Synoptics, Cambridge, UK).

FIG. 1 shows the CIEX profiles for anti-CD20 (a) and anti-CD38 (b) antibodies. cIEF analysis (FIGS. 1c and 1d) clearly shows that three IgG charge variants, containing zero, one or two C-terminal lysines per IgG molecule (K0, K1 and K2) are present in unfractionated anti-CD20 and anti-CD38 antibody preparations. Variants could be separated by CIEX as shown in the cIEF profiles of the collected isoforms. SDS PAGE analysis (FIGS. 1e and 1f) shows that structural integrity was maintained after CIEX fractionation. Only the K0 isoform was present after carboxypeptidase B (CPB) treatment of unfractionated anti-CD20 and anti-CD38 preparations, as well as in collected isoforms (FIGS. 1c and 1d).

Example 2: Binding Capacity and Induction of Complement-Mediated Cytotoxicity (CDC) by C-Terminal Lysine Isoforms of Anti-CD20 and Anti-CD38 Antibodies Antibody preparations and collected isoforms, with or without carboxypeptidase B (CPB) treatment, were obtained by preparative CIEX as described supra. Binding of antibody samples to Daudi cells, which express both CD20 and CD38, was analyzed by FACS analysis. $10^5$ cells were incubated in 50 µL in polystyrene 96-well round bottom plates (Greiner bio-one 650101) with serial dilutions of antibody preparations, ranging from 0.04 µg/mL to 10 µg/mL, in RPMI1640/0.2% BSA at 4° C. for 30 min. After washing twice in RPM1/0.2% BSA, cells were incubated with fluorescein isothiocyanate (FITC)-conjugated rabbit anti-human IgG (F0056, Dako, Glostrup, Denmark) at 4° C. for 30 min. Cells were washed twice in RPM1/0.2% BSA, resuspended in RPM1/0.2% BSA, and analyzed on a FACS Calibur™ (BD Biosciences). Binding curves were analyzed using non-linear regression (sigmoidal dose response with variable slope) using GraphPad Prism V5.01 software (GraphPad Software, San Diego, Calif., USA). To test induction of CDC, Daudi cells ($2\times10^6$ cells/mL) were incubated with serial dilutions of antibody preparations at RT for 15 min. Normal human serum (NHS; M0008, Sanquin, Amsterdam, The Netherlands) was added as a source of complement (final concentration 20% [v/v]). After incubation in round-bottom 96-well plates (Nunc™, Rochester, N.Y.) at 37° C. for 45 min, the reaction was stopped by placing the samples on ice. Cell lysis was determined by FACS analysis using propidium iodide (PI, Sigma Aldrich, Zwijndrecht, The Netherlands) staining method. % lysis was determined as follows: % lysis=(number of PI pos cells/total number of cells)×100%.

TABLE 1

Induction of CDC by anti-CD20 and anti-CD38 antibodies. Data shown are $EC_{50}$ values [µg/mL] for induction of CDC of Daudi cells by unfractionated and collected K2 isoforms, with and without carboxypeptidase B (CPB) treatment, of anti-CD20 and anti-CD38 antibodies.

|  | Unfract. | Unfract. + CPB | K2 | K2 + CPB |
|---|---|---|---|---|
| anti-CD20 | 0.84 | 0.82 | 1.8 | 1.0 |
| anti-CD38 | 0.12 | 0.13 | 0.20 | 0.16 |

FIG. 2 upper left panel shows that binding to Daudi cells of unfractionated and collected K2 isoforms of anti-CD20 antibody with and without carboxypeptidase B treatment are comparable. The upper right panel shows that the same is true for anti-CD38. The lower left panel and Table 1 show that induction of CDC is less efficient (~factor 2 less) for the collected K2 isoforms of anti-CD20 antibody. Capacity to induce CDC was restored after carboxypeptidase B treatment of the collected K2 isoforms of anti-CD20. The lower right panel and Table 1 show that the same is true for anti-CD38 antibody. Carboxypeptidase B treatment partially restored the capacity to induce CDC of the K2 isoforms. These data suggest that the presence of C terminal lysines negatively influences the capacity of an antibody to induce CDC.

Carboxypeptidase B treatment did not affect the capacity of either unfractionated anti-CD20 or anti-CD38 antibody to induce CDC. The unfractionated antibody preparations do contain C-terminal lysine isoforms (K1 and K2), as shown in FIG. 1. However, the fraction of C-terminal lysine containing isoforms in the unfractionated antibody preparations is probably too small to influence the capacity to induce CDC.

Example 3: Efficacy of C1q Utilization by Unfractionated and Collected K2 Isoforms of Anti-CD38 Antibody Antibody preparations and collected K2 isoforms, with or without carboxypeptidase B (CPB) treatment, were obtained as described supra. To test efficacy of C1q utilization, Daudi cells ($2\times10^6$ cells/mL) were incubated in RPMI1640 medium, supplemented with 10% fetal bovine serum, with a fixed concentration (10 µg/mL) of antibody preparations at RT for 15 min. C1q-depleted serum (Quidel, San Diego, Calif.) supplemented with 1 mM $MgCl_2$ and 1 mM $CaCl_2$ and low concentrations of C1q (Complement Technologies, Tyler, Tex.) was added as a source of complement (final concentration 50% [v/v]). The CDC assay was performed as described supra.

TABLE 2

Efficacy of C1q utilization by unfractionated and collected K2 isoforms of anti-CD38 antibody. Data shown are $EC_{50}$ values [µg/mL] for C1q requirement for induction of CDC of Daudi cells by unfractionated and collected K2 isoforms, with and without CPB treatment, of anti-CD38 antibody.

|  | Unfract. | Unfract. + CPB | K2 | K2 + CPB |
|---|---|---|---|---|
| anti-CD38 | 1.3 | 0.8 | 4.8 | 0.7 |

FIG. 3 and Table 2 show that the amount of C1q required to induce CDC of Daudi cells was highly increased (>3.5×) for the collected K2 isoforms of anti-CD38. Efficacy of C1q use was completely restored by carboxypeptidase B treatment. Carboxypeptidase B treatment of unfractionated anti-CD38 antibody only slightly (<2×) improved the efficacy of C1q utilization.

Example 4: Binding and CDC Induction by HEK-Produced Anti-CD38 Antibody and Mutants Containing One, Two or Three C-Terminal Lysines or a C-Terminal Glutamic Acid Per Heavy Chain To further verify that indeed the presence of C-terminal lysines was responsible for the decreased efficacy of CDC induction by the collected K2 isoform compared with the unfractionated antibody preparation, mutants were constructed containing zero, one, two or three C-terminal lysines in each heavy chain. Furthermore, a mutant with a negative charge at the C-terminus (glutamic acid; E) was constructed. Mutants are described in the table below. Amino acid P445 in EU-numbering corresponds to the proline at position 328 in SEQ ID NOS:1 and 5 (IgG1m (za) and IgG1m(f) allotype Fc-sequences, respectively).

TABLE 3

Mutants of anti-CD38 antibody.
pI values were determined by cIEF analysis (FIG. 4a).

| C-terminal sequence (using EU numbering) | Abbreviation | Charge | pI value of mutated protein |
|---|---|---|---|
| 445-PGE-447 | E2 | − | 8.2 |
| 445-PG-446 | K0 | 0 | 8.5 |
| 445-PGKP-448 | K2 | + | 8.8 |
| 445-PGKKP-449 | K4 | + + | 9.0 |
| 445-PGKKKP-450 | K6 | + + + | 9.1 |

Mammalian expression vectors for the expression of anti-CD38 antibody 005 (described in WO 2006099875 (Genmab)) were constructed by cloning the coding regions for the human IgG1 (allotype f) heavy and the kappa light chain of the antibody in pcDNA3.3 (Invitrogen). PCR was used to introduce the C-terminal heavy-chain extensions -KP, -KKP, -KKKP and -E in the heavy-chain expression vector. Proline was introduced to prevent cleavage of the added C-terminal lysine(s). All anti-CD38 antibody mutants were produced, under serum-free conditions, using Freestyle™ M medium (Invitrogen, Carlsbad, Calif.) by transiently co-transfecting relevant heavy and light chain expression vectors in HEK293F cells (Invitrogen) using 293Fectin™ (Invitrogen), according to the manufacturer's instructions. Antibodies were purified by Protein A affinity chromatography (MabSelect™ SuRe™, GE Healthcare, Uppsala, Sweden), dialyzed O/N to PBS and filter-sterilized over 0.2 μM dead-end filters. Concentrations of purified C-terminal IgG1 variants were determined by absorbance at 280 nm. Anti-CD38 antibody and anti-CD38 antibody mutants were analyzed by CIEF, binding to Daudi cells was analyzed by FACS analysis and induction of CDC was tested in a CDC assay with Daudi cells, all assays were performed as described supra.

TABLE 4

CDC induction by anti-CD38 antibody and mutants.

| | anti-CD38 | K0 | K2 | K4 | K6 | E2 |
|---|---|---|---|---|---|---|
| $EC_{50}$ | 0.21 | 0.21 | 0.29 | N.D.[a] | 0.28 | 0.26 |
| Max. lysis | 97 | 95 | 65 | 9 | 25 | 26 |

[a] could not be determined.

Data shown are $EC_{50}$ values (μg/mL) and percentage lysis induced at the highest concentration of antibody tested (4 μg/mL).

FIG. 4a shows that all antibody mutants migrated at the pI calculated based on the amino acids introduced, indicating that the mutants are stable and that the additional C-terminal amino acids were not cleaved. FIG. 4b shows that binding of anti-CD38 antibody to Daudi cells was not affected by the introduction of C-terminal lysines or the glutamic acid and was comparable for all mutants. FIG. 4c and Table 4 show that induction of CDC of Daudi cells was similar for anti-CD38 antibody and PG mutant. Introduction of one C-terminal lysine, which has a positive charge, per heavy chain, decreased the capacity to induce CDC, reflected in a lower percentage of maximal lysis (~30% decrease) induced. Introduction of two C-terminal lysines (KK) per heavy chain totally abolished the capacity to induce CDC. The mutant containing three C terminal lysines per heavy chain was slightly more efficient in induction of CDC than the mutant containing two C-terminal lysines. The mutant containing C-terminal glutamic acid was inefficient in inducing CDC as well.

Example 5: CDC Induction by Mixtures of Anti-CD38 Antibody Mutants

To investigate whether charge repulsion between IgG molecules is responsible for the reduced CDC activity of anti-CD38 mutants carrying lysine or glutamic acid at the C-terminus, mutants with different charges at the C-terminus were mixed. The CDC assay was performed as described supra.

Figure 5A:
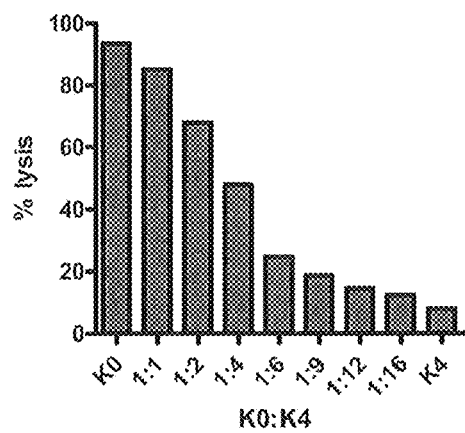
Figure 5B:
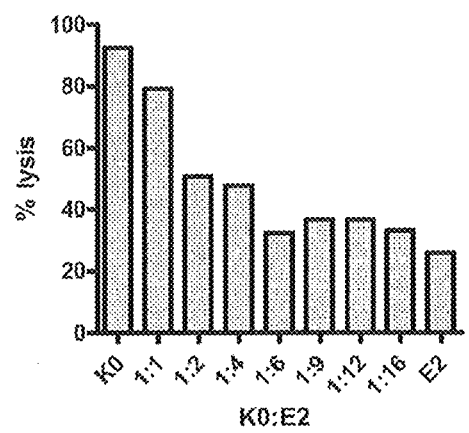
Figure 5C:
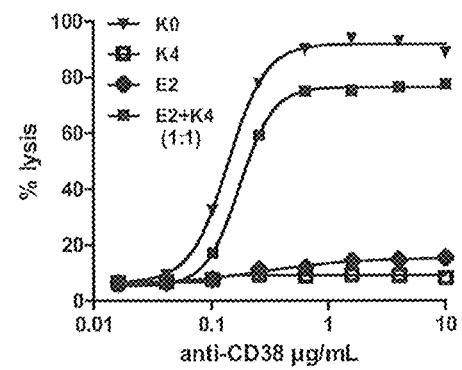
Figure 5D:
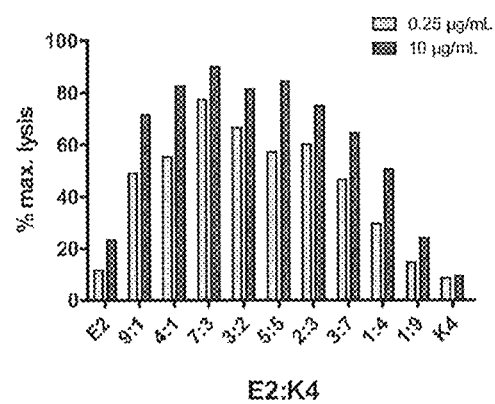

FIG. 5a shows that adding K4 mutant to K0, while keeping the total IgG concentration constant, decreased the efficacy of CDC induction, compared with that of K0 alone. FIG. 5b shows that the same effect was observed for addition of the E2 mutant. These experiments are in good agreement with our previous findings and confirm that mutants of anti-CD38 with charged residues at their C-terminus have strongly reduced CDC activity. FIG. 5c shows that mixing the negatively charged E2 mutant with the positively charged K4 mutant almost fully restored efficacy of CDC induction, to the level of CDC induced by K0. Similar results were obtained for a mixture of E2 mutant and K2 mutant (data not shown). FIG. 5d shows that maximal lysis was obtained at an E2:K4 ratio of approximately 7:3.

The data suggest that interaction between different IgG molecules, and more specifically Fc-Fc interaction, plays an important role in the induction of CDC.

Example 6: Identification of IgG1 Mutations Stimulating Fc:Fc Interaction-Mediated Antibody Oligomerization Detected by a CDC Assay A library of mutations was generated, including those focused at the C-terminal of the CH3 domain. Mutations were introduced into the IgG1 Fc-region of anti-CD38 antibody 005 using the Quikchange® site-directed mutagenesis kit (Stratagene, US). Briefly, for each desired mutation position, a forward and a reverse primer encoding a degenerate codon at the desired location were used to replicate full length plasmid DNA template. The resulting DNA mixtures were digested using DpnI to remove source plasmid DNA and used to transform E. coli. Resulting colonies were pooled, cultured and plasmid DNA was isolated from these pools and retransformed into E. coli to obtain clonal colonies. Mutant plasmid DNA isolated from resulting colonies was checked by DNA sequencing (LGC genomics, Berlin, Germany). Expression cassettes were amplified from plasmid DNA by PCR and DNA mixtures containing both a mutant heavy and a wild type light chain of anti-CD38 antibody 005 were transiently transfected to Freestyle™ HEK293F cells (Invitrogen, US) using 293Fectin™ (Invitrogen, US) essentially as described by the manufacturer. Supernatants of transfected cells containing antibody mutants were collected.

CDC assays were performed as follows. $0.1 \times 10^6$ Daudi or Wien 133 cells were pre-incubated in round-bottom 96-well plates with 1.0 µg/mL unpurified antibodies in a total volume of 100 µL for 15 min on a shaker at RT. Next, 30 µL normal human serum was added as a source of complement (30% final concentration) and incubated in a 37° C. incubator for 45 min. The reaction was stopped by putting the plates on ice. 10 µL propidium iodide was added and cell lysis was determined by FACS.

Mutations in the CH3 C-terminal region incorporated in the anti-CD38 antibody were tested for their ability to induce CDC of Daudi cells. The lytic effect of the mutant antibody was compared to that of wild type antibody, for which lysis was set to 100%. The cut-off for inhibition was set to 66% lysis. The results are shown in Table 5.

Mutations incorporated in the anti-CD38 antibody 005 were tested for their ability to enhance oligomerization as determined by CDC on Wien 133 cells. Wild type antibody is not able to induce CDC on Wien 133 cells. Mutants displaying ≥0% cell lysis were scored as enhancing. The results are shown in Table 6.

Table 5 shows that introduction of a negative charge at the C-terminus for mutations P445D and P445E, which decrease CDC when compared to the IgG1 wildtype, in line with expectations. Similarly, introduction of a positive charge, i.e. P445H and P445K, decreases CDC in line with expectations. The mutation K447I, however, apparently decreases CDC, whereas removal of the C-terminally positively charged K was expecting to have a positive impact on CDC. In addition, replacement of G446 and K447 with arginine seems to have a small positive effect on CDC, contrary to expectations. However, this assumes that the C-terminal arginine is, in fact, present on the mutants. In both cases, the arginine mutants may actually have been C-terminally cleaved, resulting in mutants lacking C-terminal charge (the theoretic c-terminal sequence of the K447R mutant is PGR, which may be cleaved to PG, and the theoretic c-terminal sequence of the G446R mutant is PRK, which may be cleaved to P).

TABLE 5

CDC induction by mutants - Daudi cells.

| | Residue | | | | | | | | | | | | | | | | | | | |
|---|---|---|---|---|---|---|---|---|---|---|---|---|---|---|---|---|---|---|---|---|
| | A | C | D | E | F | G | H | I | K | L | M | N | P | Q | R | S | T | V | W | Y |
| P445 | 75 | 94 | 25 | 22 | 95 | 60 | 41 | | 43 | 77 | | | | | | | 65 | 84 | | |
| G446 | | | | | | 72 | | | 56 | 63 | 83 | | | | 84 | | | 57 | 88 | |
| K447 | | | | | | | 92 | 28 | | 70 | | | | 71 | 80 | | | 77 | 96 | |

Percentage lysis of Daudi cells in the presence of 1.0 ug/ml anti-CD38 antibody point mutants. Wildtype antibody lysed 66% of cells under these conditions.

TABLE 6

CDC induction by mutants - Wien 133 cells.

| | Residue | | | | | | | | | | | | | | | | | | | |
|---|---|---|---|---|---|---|---|---|---|---|---|---|---|---|---|---|---|---|---|---|
| | A | C | D | E | F | G | H | I | K | L | M | N | P | Q | R | S | T | V | W | Y |
| P445 | 3 | 5 | 2 | 2 | 4 | 2 | 4 | | 4 | 3 | | | | | | | 2 | 3 | | |
| G446 | | | | | | 3 | | | 4 | 5 | 4 | | | | 7 | | | 3 | 7 | |
| K447 | | | | | | | 3 | 4 | | 3 | | | | 3 | 2 | | | 2 | 6 | |

Percentage lysis of Wien 133 cells in the presence of 1.0 ug/ml anti-CD38 antibody point mutants. Wildtype antibody lysed 3% of cells under these conditions.

The invention claimed is:

1. An isolated IgG antibody comprising a heavy chain comprising at the C-terminus an amino acid sequence selected from the group consisting of: PGE, SEQ ID NO: 6, SEQ ID NO: 7, and SEQ ID NO: 8, wherein said amino acid sequence inhibits proteolytic removal by a mammalian protease.

2. The antibody according to claim 1, further comprising a light chain.

3. The antibody according to claim 1, wherein the antibody induces complement-dependent cytotoxicity to a lesser extent compared to an antibody lacking said amino acid sequence.

4. The antibody of claim 1, wherein the amino acid sequence at the C-terminus comprises the sequence PGE.

5. The antibody of claim 1, wherein the amino acid sequence at the C-terminus comprises SEQ ID NO: 6.

6. The antibody of claim 1, wherein the amino acid sequence at the C-terminus comprises SEQ ID NO: 7.

7. The antibody of claim 1, wherein the amino acid sequence at the C-terminus comprises SEQ ID NO: 8.

8. The antibody of claim 1, wherein, other than said amino acid sequence, the IgG antibody is an isotype selected from the group consisting of: IgG1, IgG2, IgG3, and IgG4.

9. The antibody of claim 1, wherein the protease is selected from a protease of CHO, HEK293, PER.C6, NSO, or Sp2/0 cell origin.

10. The antibody of claim 1, wherein the protease is a carboxypeptidase.

11. A nucleotide construct encoding an IgG heavy chain comprising at the C-terminus an amino acid sequence selected from the group consisting of: PGE, SEQ ID NO: 6, SEQ ID NO: 7, and SEQ ID NO: 8, wherein said amino acid sequence inhibits proteolytic removal by a mammalian protease.

12. The nucleotide construct according to claim 11, further encoding a light chain.

13. The nucleotide construct of claim 11, wherein the amino acid sequence at the C-terminus comprises the sequence PGE.

14. The nucleotide construct of claim 11, wherein the amino acid sequence at the C-terminus comprises SEQ ID NO: 6.

15. The nucleotide construct of claim 11, wherein the amino acid sequence at the C-terminus comprises SEQ ID NO: 7.

16. The nucleotide construct of claim 11, wherein the amino acid sequence at the C-terminus comprises SEQ ID NO: 8.

17. The nucleotide construct of claim 11, wherein, other than said amino acid sequence, the IgG antibody is an isotype selected from the group consisting of: IgG1, IgG2, IgG3, and IgG4.

18. The nucleotide construct of claim 11, wherein the protease is selected from a protease of CHO, HEK293, PER.C6, NSO, or Sp2/0 cell origin.

19. The nucleotide construct of claim 11, wherein the protease is a carboxypeptidase.

20. A isolated recombinant host cell which produces the antibody of claim 1, wherein the recombinant cell is genetically engineered to produce glycoproteins having human-like or human glycosylation.

21. A method for producing an IgG antibody comprising a heavy chain comprising at the C-terminus an amino acid sequence selected from the group consisting of: PGE, SEQ ID NO: 6, SEQ ID NO: 7, and SEQ ID NO: 8, wherein said amino acid sequence inhibits proteolytic removal by a mammalian protease, the method comprising culturing the host cell according to claim 20 and recovering said antibody from the cell culture.

22. The method according to claim 21, wherein said host cell is a CHO or HEK cell.

23. An isolated IgG antibody comprising a heavy chain comprising at the C-terminus an amino acid sequence selected from the group consisting of: PGE, SEQ ID NO: 6, SEQ ID NO: 7, and SEQ ID NO: 8, wherein said amino acid sequence inhibits proteolytic removal by a mammalian protease, and wherein the antibody induces complement-dependent cytotoxicity to a lesser extent compared to an antibody lacking said amino acid sequence.

\* \* \* \* \*

UNITED STATES PATENT AND TRADEMARK OFFICE
CERTIFICATE OF CORRECTION

| | | |
|---|---|---|
| PATENT NO. | : 11,795,214 B2 | Page 1 of 1 |
| APPLICATION NO. | : 16/399424 | |
| DATED | : October 24, 2023 | |
| INVENTOR(S) | : Parren et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 137 days.

Signed and Sealed this
Nineteenth Day of August, 2025

Coke Morgan Stewart
*Acting Director of the United States Patent and Trademark Office*